United States Patent [19]

Coupland et al.

[11] Patent Number: 6,077,994
[45] Date of Patent: Jun. 20, 2000

[54] GENETIC CONTROL OF FLOWERING

[75] Inventors: George M. Coupland, Colney, United Kingdom; Joanna J. Putterill, Auckland, New Zealand

[73] Assignee: Plant Bioscience Limited, Norwich, United Kingdom

[21] Appl. No.: 08/945,056

[22] PCT Filed: Nov. 1, 1995

[86] PCT No.: PCT/GB95/02561

§ 371 Date: Oct. 20, 1997

§ 102(e) Date: Oct. 20, 1997

[87] PCT Pub. No.: WO96/14414

PCT Pub. Date: May 17, 1996

[30] Foreign Application Priority Data

Nov. 2, 1994 [GB] United Kingdom .................. 9422083

[51] Int. Cl.[7] .......................... C12N 15/29; C12N 15/82; C12N 5/04; A01H 5/00
[52] U.S. Cl. ........................ 800/290; 536/23.6; 435/69.1; 435/320.1; 435/419; 435/440; 435/468; 800/276; 800/298; 800/306
[58] Field of Search .................... 536/23.6; 435/69.1, 435/320.1, 419, 440, 468; 800/276, 290, 298, 306

[56] References Cited

U.S. PATENT DOCUMENTS 5,589,614 12/1996 Bridges et al. ........................ 800/205

OTHER PUBLICATIONS

Molecular and General Genetics, vol. 239, 1993 Berlin, DE, pp. 145–157, Putterill, J., et al, Chromosome walking with YAC clones in Arabidopsis: isolation of 1700 kb of contiguous DNA cjhromosome 5, including a 300kb region containing the flowering–time gene CO.

The Plant Journal, vol.. 5, No. 2, Feb. 1994 pp. 261–272, Wester, L., et al., "Transgenic complementation of the hy3 phytochrome B mutation and response to PHYB gene copy number in Arabidopsis".

Plant Molecular Biology, vol. 26, Oct. 1994 pp. 657–665, Chung, Y–Y., et al., "Early flowering and reduced apical dominance result from ectopic expression of a rice MADS box gene".

Cell, vol. 80, Mar. 24, 1995 pp. 847–857, Putterill, J., et al., "The Constans gene of Arabidopsis promotes flowering and encodes a protein showing similarities to zinc finger transcription factor".

Plant Molecular Biology, vol. 25, Jun. 1994 pp 335–337, AN, G., "Regulatory genes controlling flowering time or floral organ development".

The Plant Cell, vol. 6, No. 1, Jan. 1994 pp. 75–83, Lee, I., et al., "Isolation of Luminidependens: a gene involved in the control of flowering time in Arabidopsis".

The Plant Cell, vol. 6, No. 1, Jan. 1994 pp. 1–3, CHASAN, R., "A time to flower".

Database WP1, Section Ch, Week 9243 Derwent Publications Ltd., London, GB; Class C06, AN 92–354683 & JP, A, 04 258 292 (Japan Tobacco Inc), Sep. 14, 1992.

EMBL Sequence Database Rel.41, Sep. 24, 1994, Accession No. Z37717, Morris, P.C., et al., "A thaliana transcribed sequence; clone YBY029; 5'end".

Hybond™ N+; positively charged nylon membrane. Amersham Life Science, Amersham: UK, pp. 1–8, 1992.

Barsby et al. Plant Cell Reports 5:101–103, 1986.

Law et al. pp. 47–68 In: Mol. Biol. Flowering, Jordan, B., ed., CAB: Wallingford, UK, 1993.

*Primary Examiner*—David T. Fox
*Attorney, Agent, or Firm*—Nixon & Vanderhye P.C.

[57] ABSTRACT

The CONSTANS (CO) gene of *Arabidopsis thaliana* and homologues from *Brassica napus* are provided and are useful for influencing flowering characteristics in transgenic plants, especially the timing of flowering.

24 Claims, 9 Drawing Sheets

```
  1  ATGTTGAAACAAGAGAGTAACGACATAGGTAGTGGAGAGAACAACAGGGCACGACCCTGT
     M  L  K  Q  E  S  N  D  I  G  S  G  E  N  N  R  A  R  P  C

61  GACACATGCCGGTCAAACGCCTGCACCGTGTATTGCCATGCAGATTCTGCCTACTTGTGC
     D  T  C  R  S  N  A  C  T  V  Y  C  H  A  D  S  A  Y  L  C

121  ATGAGCTGTGATGCTCAAGTTCACTCTGCCAATCGCGTTGCTTCCCGCCATAAACGTGTC
     M  S  C  D  A  Q  V  H  S  A  N  R  V  A  S  R  H  K  R  V

181  CGGGTCTGCGAGTCATGTGAGCGTGCTCCGGCTGCTTTTTTGTGTGAGGCAGATGATGCC
     R  V  C  E  S  C  E  R  A  P  A  A  F  L  C  E  A  D  D  A

241  TCTCTATGCACAGCCTGTGATTCAGAGGTTCATTCTGCAAACCCACTTGCTAGACGCCAT
     S  L  C  T  A  C  D  S  E  V  H  S  A  N  P  L  A  R  R  H

301  CAGCGAGTTCCAATTCTACCAATTTCTGGAAACTCTTTCAGCTCCATGACCACTACTCAC
     Q  R  V  P  I  L  P  I  S  G  N  S  F  S  S  M  T  T  T  H

361  CACCAAAGCGAGAAAACAATGACCGATCCAGAGAAGAGACTGGTGGTGGATCAAGAGGAA
     H  Q  S  E  K  T  M  T  D  P  E  K  R  L  V  V  D  Q  E  E

421  GGTGAAGAAGGTGATAAGGATGCCAAGGAGGTTGCTTCGTGGCTGTTCCCTAATTCAGAC
     G  E  E  G  D  K  D  A  K  E  V  A  S  W  L  F  P  N  S  D

481  AAAAATAACAATAACCAAAACAATGGGTTATTGTTTAGTGATGAGTATCTAAACCTTGTG
     K  N  N  N  N  Q  N  N  G  L  L  F  S  D  E  Y  L  N  L  V

541  GATTACAACTCGAGTATGGACTACAAATTCACAGGTGAATACAGTCAACACCAACAAAAC
     D  Y  N  S  S  M  D  Y  K  F  T  G  E  Y  S  Q  H  Q  Q  N

601  TGCAGCGTACCACAGACGAGCTACGGGGGAGATAGAGTTGTTCCGCTTAAACTTGAAGAA
     C  S  V  P  Q  T  S  Y  G  G  D  R  V  V  P  L  K  L  E  E

661  TCAAGGGGCCACCAGTGCCATAACCAACAGAATTTTCAGTTCAATATCAAATATGGCTCC
     S  R  G  H  Q  C  H  N  Q  Q  N  F  Q  F  N  I  K  Y  G  S

721  TCAGGGACTCACTACAACGACAATGGTTCCATTAACCATAACGCATACATTTCATCCATG
     S  G  T  H  Y  N  D  N  G  S  I  N  H  N  A  Y  I  S  S  M

781  GAAACTGGTGTTGTGCCGGAGTCAACAGCATGTGTCACAACAGCTTCACACCCAAGAACG
     E  T  G  V  V  P  E  S  T  A  C  V  T  T  A  S  H  P  R  T

841  CCCAAAGGGACAGTAGAGCAACAACCTGACCCTGCAAGCCAGATGATAACAGTAACACAA
     P  K  G  T  V  E  Q  Q  P  D  P  A  S  Q  M  I  T  V  T  Q

901  CTCAGTCCAATGGACAGAGAAGCCAGGGTCCTGAGATACAGAGAGAAGAGGAAGACAAGG
     L  S  P  M  D  R  E  A  R  V  L  R  Y  R  E  K  R  K  T  R

961  AAATTTGAGAAGACAATAAGGTATGCTTCGAGGAAGGCATATGCAGAGATAAGACCGCGG
     K  F  E  K  T  I  R  Y  A  S  R  K  A  Y  A  E  I  R  P  R

1021 GTCAATGGCCGGTTCGCAAAGAGAGAAATCGAAGCCGAGGAGCAAGGGTTCAACACGATG
     V  N  G  R  F  A  K  R  E  I  E  A  E  E  Q  G  F  N  T  M

1081 CTAATGTACAACACAGGATATGGGATTGTTCCTTCATTCTGATA
     L  M  Y  N  T  G  Y  G  I  V  P  S  F  *
```

Fig. 1

```
   1  AAGCTTGGGC GTAGGTGTTG TCTATCGGCG AAAACACGCG CGGTACGCCA
  51  AGAACAGCGC GGCCATCTCC ATCCCAGGCA CGGTGCGCCC GCTTTTTCGC
 101  CGTCTCGCTG AGTCACGGCG GGCGTCCAGC AGGTAGTTGA GCGCCTTCCG
 151  CGGCACGAAT CGCTGCGTGC GGCCCGGATC TGGTCGAGTT GGTAGTCAGC
 201  GTCGGTGTCG AATGCCGGGA CGTCGACCAG GAAGAAGTTG CCGTCGCTGG
 251  GGTGGGGACG GAAGGCGTCA GGATTGTCGC AAGGGCAGAG CCCAGCCTGC
 301  GGGCGGGGCT ACCTCGTCGA CGCCTCGGCA CGGCGGCGGC AAAGCTGCTG
 351  CGGGACGTGC CCGCCTGGGC CGCCTTCTCG GTGAAGTGGT CCTCGAAGGG
 401  GACGAGCTCG CTGGGGTCAA ACCACCCCAT AGCTCGAGTC ACCGAAGAAG
 451  GCGACGAGGA CGAGCCCGTC GCGGTGGCCG CGGTGTACCT CCTCGTCGTC
 501  GGTGAGGCTG ACGCTGTAGA TATGGCCAGG CCACCACGGA TGGGACTTCA
 551  CCTTGGCCCA GACCATGTCG CCGAACCGGG GGCCGCCGTT CGCCCATGCG
 601  ATGCCGCGTC CGGCAGCAGG AACCATGGCG CCTCCAGCGG CGGGGTCGGA
 651  CATCCTGTGG AGGGGAACCG AAAACCTAGA TTTGGATGCA GGTTCGATTG
 701  GTCTGGGCTT GGGTTTGGGT TCCGGAGGAG GGTGGCCTGG GATCGGTGGA
 751  AGGAGGGACA TTGTTGGTAA TTTTTATTAT TTTATAATAT GGAGAAATTC
 801  GAGAGACTGA ACGATGGTGA TGTTTATTTG AGGACTATGT AGTATAAAGT
 851  GTAAAATAGT ATTTTATCAA GTTTATATTC ACGTTTTTGC TGAAGATAGT
 901  ATAATAGTGG AGTTGTTTTT GGCGGCTACA TAATCTTAGG CTATCTTCTC
 951  GGTCGCTCTC ATATCATATC TACTATCACA TTCTCTATTT TAAATTTCAC
1001  TTTGTGTAAT CTACACTATA AAATAGTGTT TTACACGGTA TGTTGTACAC
1051  AGCCTTATCG TGGCGCGACG GAGTTGGATA GAGATGGTGA ACAGCTGGAT
1101  AGATATGATT TATAGGCGAT TGGGTAGATG TGATTTGATA GGTGGTTATG
1151  TAGGAGCGAT TTAGTGAGAC ATTGTAAATA ATTAGGTTGA TGTGATCCGA
1201  GGATGGCTAG GTAGATATGA TTTTAATGGA TGGTTTGGTG GACTAAGTTA
1251  TGTGGACATT ATAATATGTT TTAAATTTCT AAGAAATTGT TTGTGTTAAA
1301  TTGTATCCCA CATAGATTAT TTAGCCATCT CAAAGAGAGG TTTGGGTTGT
```

Fig. 2A

```
1351  TTACACAAAT AAAATATTCG TTTGCTTCTA CAATTTATAT GTTTTTTATT
1401  TACATGAAAA CTATATTTTT TATTCATCTA CTCACCCAGC ACAGAAATTC
1451  TGGTTGAGTA GATGAAAAAA AACTACAACA AACTCTTCCT GAAAGTGTCG
1501  GTGTGAAGCC GAGAAATCCT TTTCATTTCG GTGACGGAGC CCCTTGCTGG
1551  CTGCTGCTCA GTGCACTCCG TTCGCCTGCC TGCCACTACA AGCGACGGCC
1601  GACGACTCGC AAGTATCGGT AGGCATTTTA AAACTGAAAA CCAAATCTAA
1651  ACCCGAATAG ACCAAATTGT TGGTTTATTC GGGTTTTTGG GTTCGGATTC
1701  GGTTTCTAAA TATGCTATAT TTTAGGGTAT AGGTTCGGGT TCAGTTTCTA
1751  ACCTTTAAAA CCTGAATAGA CGAATAACCC GAAATATAAA AAATCTCTTA
1801  ATATGTGATG ATATTATTAT ATGATTTATG AACTTATTAA CCGAAAATAA
1851  TGATACCATC CTAACGATAG TATATATATC TATGTATGCT ATTTTTATAG
1901  TCACTTGTTG TAATAATAGT ACTTCCAATT AATTAATCAG TGTATATATT
1951  TTAACAAAAG ATACTAGCCT CTCTACTATT TGAGTATATT CGGTGCACCG
2001  AATAGACCGA ACCGAAATTG TAAGTCTATT CAGGTTCGGT TCCTAAAATT
2051  ATTTTAAAAA TTTTGGTTCT CATATTTCAG AATCCGAAAT TTCATAAATC
2101  CAAATAGACC GAACCAAATT ACGCTAATAG ACCGAATAAC TAGCGTACTC
2151  GCAAGTCGCA CCCCACTAGC CTGCTGCGTG CGTAAGCGAG GACGTCACGC
2201  GTTCTCCCTC CCGTCGACCA AATACACTTG GTCTTCTAGC ACCTTCTTCC
2251  TCTCCAAGAC TCCAATCCCC CAACCACCAG AACCAGCGCC AGCTCTAACG
2301  TCACCTCTGA TTTCTCTCTC CTCTCTATTG CTAGCTGCTT TATTATAAGT
2351  AGCAGCTGCA GCAGGCAGGA GCTGCACACA CCCATCCAAT TCCAGCTGCT
2401  GATCTTGATC CTGCACCCCG AGCCGTACAC AAGAGCTAGT CGGTAGAACT
2451  TGCAGGAGCG GAGCAGAACT AAGTGCAGAG AACAGGACAT ATG
```

Fig. 2B

```
   1  GAATTCATGT ACCAAATCAA TACTTTTTAG CCATAAATGA GTCAGTTTTA
  51  GTATCCACAT GAATTTACCT ACCAGAGTGT TGTAAATTAT GTTCTTTTGG
 101  GGCCACTTAC ATGGATCTCA TTCATTCACT GCAGCGAGTT CTCAGACCAC
 151  CAGAAAATTT ATTCAGTGAT CTGTTTTGAT CATGCAACAT AAACTTATAA
 201  GCCACACAAG CAAAACAAAG ATATCCCATG TTGCATATAA TACGAGCTAG
 251  CATATCATAA AGAAGGAAAC TTGAAGTAGC AAAGTTTCTA CTAAATTTCT
 301  TGTCAGGAAT TTTTAAAATG CAATGACAAC CACTTGGAGC ACTATGAGTT
 351  TCAGAGCCAA TAGAATGTTA CTATTTGGTG TGGATTCGAG CTAGCACGTG
 401  AAAGTGCATA AAAGTGATTA CCTTTTGCCA AAGGTCACTG CACTTTTCCT
 451  CAGATAGTTT CTCACAGCCA TGGAAAGTGG AGAATCCGCA TAAACGTACA
 501  ATTACAAGCT TTATATGGTC CCTCGACTCT TATTCTCTTC TCAGTCTTTG
 551  CAACTAAATA GGGTTTTCGT TAATCTGAAA GAAGCAAAGT ATTCGAAACC
 601  ACGGAAACCT GATAAAGAAT GAAAACAAAT AAGCAATAGT GTTTTCTTGA
 651  AAATCTCGAT GCAACTTTGA GGATATTGTT ACATATGATC TATTACTCGT
 701  AACAGTTATC CGAAGGCCTA CACATGTGAG AGAAGTTCCA AACCGCTACA
 751  ACAATAAACT TAATTAGAGA CTGTCAACGA GCAATAATAA GCAAAACTAC
 801  TTTTTTCTTG AGCTACAAGT GAAAAGGCCA ATACACAATT TACTCTTCAT
 851  GAACTCGAAC CACGTTACAA TCTCCAAAAA ATTTCATCAC CAAAGCACTA
 901  AAAGCCAAAG ATGCCTCAAC TTATCCAACT TGGCAGGATA AAGATCTCCA
 951  AAAATGCTTA CTAAAGAACC TAGAATCTTT TCTTTAGAAT TCAATGATCA
1001  TATAACCATT TCATAACAAT TCTAAATGCC ATTACATTCA TCGTAAAACC
1051  AGTAAATAAC AAGAACTTGT ATGTTAAGTT CCAATTACCA AGCAAAAAAA
1101  AACTTTTCAA AGTTTAAAGT TCAAAATGGG AAAGAGAAGT GCGGTGTAAG
1151  CAAATATGAA AGAGGAAGAG ATGCGAAAAG TGTATCCTAG GACCAGCATT
1201  TTATACAAAA AAAAAACACT CACTTTTCAG CTCTTAAGGC ATAGAGTGAA
1251  GGTAGCCATA TGAATTTGGC CACTAGAGCG TCCGTCAAAT CTCATTCTTT
1301  TTGGACCACA TAATGGGTAT CATACATTCA CTGGACCCAA AAGCGTAACT
1351  GGAGCTAGTC CTCAAACCTA GAGAGTATCG TATCCTGTAG CTTCCACATA
1401  GTAAACATTA TGAGCATAAC ACCAACAAGG CAACTCCAAG TACTAATGGT
```

Fig. 3A

| | | | | | |
|---|---|---|---|---|---|
| 1451 | TATTAGTACA | GGAAAACCCA | CGATGCTAAA | CACATGAATG | GGTCACCAAA |
| 1501 | TAGAGTGAAG | ATGGTTAAAT | TGCATCTATG | GATCATGTGG | ACTAGTAAAT |
| 1551 | GAGTGTAGCA | GAAAACTTCA | CAATTACCTC | TGTGATCTTA | GAAACATGTC |
| 1601 | CTGAAAATTC | CATACAAGTG | TCGTTTGTAT | TAGATTACTT | CCACAGGTTG |
| 1651 | AGATCTAATA | AAGCTACAAT | AAATAGTATA | GAGTATCATC | ATAAACCCAA |
| 1701 | ATTACAGAGA | TGTGACAACA | CTCATGAGTC | ATGTTTTGTA | ACTACTTACT |
| 1751 | ATAATGGTTA | CCAAGTGCAA | ATTTCTACAT | ACTATATATG | ATAAATCTAA |
| 1801 | TTATTGCTCA | TGTGGACTCC | AAAATGCCTT | TTAAGTTTTA | ACTTGTGCGT |
| 1851 | CAGGTAAATT | CTAATTTGTA | GTCTCAAGAC | TACTTGGCGG | ATTCGAGTTT |
| 1901 | GATCCTAGAA | AATCCACCGT | CTCTATGTTT | TTCATGTCAC | TTTTCCGATA |
| 1951 | TGATTCTCAT | TACCATGACT | TTATGAACCA | GATTAAACAT | TATAACACTT |
| 2001 | TTCATCAGAA | AATCCTTCGA | AAGTTTCAAT | TGCAAATCTT | TCTAAATGAT |
| 2051 | GCAGATGCAT | TCACAAATAA | TGGAACAACA | ACTATACCAT | ATTCACGAGT |
| 2101 | TTGTCTAACC | TTTGTATAGG | TAGTCAACCC | ATAACAGTTG | GTGATGGCTC |
| 2151 | TGACACTCGA | AGCCTTACTC | GGAGAGATAC | CTGAACAGTA | ATCACAAGGT |
| 2201 | TCAGGATGAA | TATTCAACCA | CTTAAACTTT | GTATAAAGCC | AAAGAGATAA |
| 2251 | AACGAATCTA | GCTTTACTTT | AAATAAAATG | CATATGAAAA | TAGTAAAAGG |
| 2301 | TGATACGAAA | AAATAGTAAC | AATTTGCCTG | CAACACCATG | GCATTATCCG |
| 2351 | GACCACTTCC | TCTTGAGAAT | CTCAGTATGG | CAAGTGGCAA | AACCTAAGCA |
| 2401 | ACTTGTGAAC | GGGTCCCAAC | GAAGAAGTGC | ATAGGAGGAG | ATGTTTACAC |
| 2451 | TTTACACTTT | ACACTTTACA | CTTTACACAT | AGGCCTTCCC | AAAAGCTCAA |
| 2501 | CTAGCTGCAA | GAGGATCCAA | TAACATGTAA | GAGCCACTAA | CGCTGTGCCA |
| 2551 | CGTGTAGGCA | CTCAGGATTC | GATCTTCCCC | TCTACTTATT | CTCTCACACC |
| 2601 | AGATATAAGC | TTTATTAGCC | CCTTCTTTCA | GATACCAGCT | CCCACACCAT |
| 2651 | CAAACTTACT | ACATCTGAGT | TATTATGTTG | AAACAAGAGA | GTAACGACAT |
| 2701 | AGGTAGTGGA | GAGAACAACA | GGGCACGACC | CTGTGACACA | TGCCGGTCAA |
| 2751 | ACGCCTGCAC | CGTGTATTGC | CATGCAGATT | CTGCCTACTT | GTGCATGAGC |
| 2801 | TGTGATGCTC | AAGTTCACTC | TGCCAATCGC | GTTGCTTCCC | GCCATAAACG |
| 2851 | TGTCCGGGTC | TGCGAGTCAT | GTGAGCGTGC | TCCGGCTGCT | TTTTGTGTG |

Fig. 3B

```
2901  AGGCAGATGA TGCCTCTCTA TGCACAGCCT GTGATTCAGA GGTTCATTCT
2951  GCAAACCCAC TTGCTAGACG CCATCAGCGA GTTCCAATTC TACCAATTTC
3001  TGGAAACTCT TTCAGCTCCA TGACCACTAC TCACCACCAA AGCGAGAAAA
3051  CAATGACCGA TCCAGAGAAG AGACTGGTGG TGGATCAAGA GGAAGGTGAA
3101  GAAGGTGATA AGGATGCCAA GGAGGTTGCT TCGTGGCTGT TCCTAATTC
3151  AGACAAAAAT AACAATAACC AAAACAATGG GTTATTGTTT AGTGATGAGT
3201  ATCTAAACCT TGTGGATTAC AACTCGAGTA TGGACTACAA ATTCACAGGT
3251  GAATACAGTC AACACCAACA AAACTGCAGC GTACCACAGA CGAGCTACGG
3301  GGGAGATAGA GTTGTTCCGC TTAAACTTGA AGAATCAAGG GGCCACCAGT
3351  GCCATAACCA ACAGAATTTT CAGTTCAATA TCAAATATGG CTCCTCACGG
3401  ACTCACTACA ACGACAATGG TTCCATTAAC CATAACGTAA GGCTTTTGTA
3451  TATTTGTTAC CCCTTCAATT TAGCATCTTC CCATAACGCA GCAGGGTGAA
3501  TTCTTTCATC ATACACACAA ATCCACTGAT CCACTGCCAA CAGTTGATCT
3551  ATAGCACATA GAAATTTCAC CAGAAGTCTA TAATAAAAAC AATATATGCT
3601  TCCTTTTGCA TCGACTCTCT TTAGTCCTCT TACCAGGGGG ATTGAGAATG
3651  TCTTTGTTTC TGTCATTAGG CATACATTTC ATCCATGGAA ACTGGTGTTG
3701  TGCCGGAGTC AACAGCATGT GTCACAACAG CTTCACACCC AAGAACGCCC
3751  AAAGGGACAG TAGAGCAACA ACCTGACCCT GCAAGCCAGA TGATAACAGT
3801  AACACAACTC AGTCCAATGG ACAGAGAAGC CAGGGTCCTG AGATACAGAG
3851  AGAAGAGGAA GACAAGGAAA TTTGAGAAGA CAATAAGGTA TGCTTCGAGG
3901  AAGGCATATG CAGAGATAAG ACCGCGGGTC AATGGCCGGT TCGCAAAGAG
3951  AGAAATCGAA GCCGAGGAGC AAGGGTTCAA CACGATGCTA ATGTACAACA
4001  CAGGATATGG GATTGTTCCT TCATTCTGAT ACTCCTGTGG CAAAAGAAA
4051  AACTAGATTG CAAGCTGTAA ATTACTTTTA GTTTGAGATT ATGTTAGGTT
4101  TGGTGAAATT CTTAGCTTCA AGAAGTATTA CTACTGTTGT GCAAATGGGT
4151  TTGTAGTTTT GGCTAATTAA AACTATAGTA TTCTTCTTTC TCTGCATTAG
4201  T
```

Fig. 3C

```
1    ATGTTCAAACAAGAGAGTAACAACATTGGTAGTGAAGAGAACAACACCGGGGCGCGAGCT
     M  F  K  Q  E  S  N  N  I  G  S  E  E  N  N  T  G  A  R  A

61   TGTGACACATGCGGGTCAACCATCTGCACCGTGTACTGCCATGCTGACTCCGCCTACTTA
     C  D  T  C  G  S  T  I  C  T  V  Y  C  H  A  D  S  A  Y  L

121  TGCAATAGCTGCGATGCTCAAGTCCACTCTGCCAATCGCGTTGCTTCCCGCCATAAAAGG
     C  N  S  C  D  A  Q  V  H  S  A  N  R  V  A  S  R  H  K  R

181  GTCAGAGTGTGCGAGTCATGTGAGCGTGCCCCTGCTGCTTTTATGTGTGAGGCAGATGAT
     V  R  V  C  E  S  C  E  R  A  P  A  A  F  M  C  E  A  D  D

241  GTGTCTCTATGCACAGCCTGTGATTCAGAGGTTCACTCCGCAAACCCTCTTGCTAGACGC
     V  S  L  C  T  A  C  D  S  E  V  H  S  A  N  P  L  A  R  R

301  CATCAGCGAGTTCCAGTTGTGCCGATAACTGGAAACTCTTGCAGCTCCTTGGCCACCGCT
     H  Q  R  V  P  V  V  P  I  T  G  N  S  C  S  S  L  A  T  A

361  AACCACACAACAGTGACCGAGCCAGAGAAGAGAGTGGTGTTAGTTCAAGAGGATGCCAAA
     N  H  T  T  V  T  E  P  E  K  R  V  V  L  V  Q  E  D  A  K

421  GAGACGGCTTCATGGTTGTTCCCTAAAAACAGTGACAATCACAACAACAACAACCAGAAC
     E  T  A  S  W  L  F  P  K  N  S  D  N  H  N  N  N  N  Q  N

481  AATGAGTTGTTGTTTAGTGATGACTATCTAGACCTTGCTGATTACAACTCGAGTATGGAC
     N  E  L  L  F  S  D  D  Y  L  D  L  A  D  Y  N  S  S  M  D

541  TACAAGTTCACTGGTCAATACAATCAACCTACTCAACATAAACAAGACTGCACCGTACCA
     Y  K  F  T  G  Q  Y  N  Q  P  T  Q  H  K  Q  D  C  T  V  P

601  GAGAAAAACTACGGTGGAGATAGAGTTGTTCCACTCCAACTTGAAGAAACAAGAGGAAAC
     E  K  N  Y  G  G  D  R  V  V  P  L  Q  L  E  E  T  R  G  N

661  TTGCACCACAAGCAACATAATATCACGTATGGCTCCTCAGGAAGTCACTACAACAACAAT
     L  H  H  K  Q  H  N  I  T  Y  G  S  S  G  S  H  Y  N  N  N

721  GGTTCCATAAACCATAACGCATACAATCCATCAATGGAAACTGACTTTGTTCCGGAGCAG
     G  S  I  N  H  N  A  Y  N  P  S  M  E  T  D  F  V  P  E  Q

781  ACAGCACCTGACAAAACAGTTTCACATCCAAAAACGCACAAAGGGAAGATAGAGAAACTA
     T  A  P  D  K  T  V  S  H  P  K  T  H  K  G  K  I  E  K  L

841  CCTGAACCTCTAATTCAGATTCTCAGTCCAATGGACAGAGAAGCTAGAGTCCTGAGATAC
     P  E  P  L  I  Q  I  L  S  P  M  D  R  E  A  R  V  L  R  Y

901  AGAGAGAAGAAGAAGAGAAGAAAGTTTGAAGAAGACAATAAGGTATGCTTCAAGGAAGCA
     R  E  K  K  K  R  R  K  F  E  K  T  I  R  Y  A  S  R  K  A

961  TATGCAGAGAGAAGACCGAGGATCAATGGACGGTTTGCAAAGATTAGTGAAACCGAAGTA
     Y  A  E  R  R  P  R  I  N  G  R  F  A  K  I  S  E  T  E  V

1021 GAGGACCAAGAGTACAACACAATGCTAATGTACTATGACACAGGATATGGCATTGTTCCT
     E  D  Q  E  Y  N  T  M  L  M  Y  Y  D  T  G  Y  G  I  V  P

1081 TCATTCTATGGCCAAAAATAA
     S  F  Y  G  Q  K  *
```

Fig. 5

```
  1 ATGTTCAAACAAGAGAGTAACAACATTTGTAATAGAGAGAACAACAGAGGGGCACGAGCC
    M  F  K  Q  E  S  N  N  I  C  N  R  E  N  N  R  G  A  R  A

61 TGTGACACATGCGGGTCAACCATCTGCACCGTGTACTGCCATGCTGACTCTGCCTACTTA
    C  D  T  C  G  S  T  I  C  T  V  Y  C  H  A  D  S  A  Y  L

121 TGCAATAGCTGCGATGCTCAAGTCCACTCTGCCAATCGCGTTGCTTCCCGCCATAAACGT
    C  N  S  C  D  A  Q  V  H  S  A  N  R  V  A  S  R  H  K  R

181 GTCCGGGTCTGCGAGTCATGTGAGCGTGCCCCTGCTGCTTTTATGTGTGAGGCAGATGAT
    V  R  V  C  E  S  C  E  R  A  P  A  A  F  M  C  E  A  D  D

241 GTGTCTCTATGCACAGCCTGTGATTTAGAGGTTCACTCCGCAAACCCTCTTGCTAGACGC
    V  S  L  C  T  A  C  D  L  E  V  H  S  A  N  P  L  A  R  R

301 CATCAGCGAGTTCCAGTTGTGCCGATAATTGGAAACTCTTGCAGCTCCTTGGCCACCGCT
    H  Q  R  V  P  V  V  P  I  I  G  N  S  C  S  S  L  A  T  A
                                           361
AACCACACAACAGTGACCGAGCCAGAGAAGAGAGTGGTGTTAGTTCAAGAGGATGCCAAA
    N  H  T  T  V  T  E  P  E  K  R  V  V  L  V  Q  E  D  A  K

421 GAGACGGCTTCATGGTTGTTCCCTAAAAACAGTGACTATCACAACAACAACAACAACCAG
    E  T  A  S  W  L  F  P  K  N  S  D  Y  H  N  N  N  N  N  Q

481 AACAATGAGTTGTTGTTTAGTGATGACTACCTAGACCTTGCTGATTACAACTCCAGTATG
    N  N  E  L  L  F  S  D  D  Y  L  D  L  A  D  Y  N  S  S  M

541 GACTACAAGTTCACCAGTCAATACAATCAACCTCGACATAAACAAGACTGCATCGTACCA
    D  Y  K  F  T  S  Q  Y  N  Q  P  R  H  K  Q  D  C  I  V  P

601 GAGAAAAACTACAGTGGAGATAGAGTTGTTCCGCTCCAACTTGAAGAAACAAGAGGAAAC
    E  K  N  Y  S  G  D  R  V  V  P  L  Q  L  E  E  T  R  G  N

661 TTGCGGAACAAGCAACAGAATATCACATATGGCTCCTCAGGAAGCCAATACAACAACAAC
    L  R  N  K  Q  Q  N  I  T  Y  G  S  S  G  S  Q  Y  N  N  N

721 GGTTCCATTAACCATAACGCATACAATCCATCAATGGAAACTGACTTTGTGCCGGAGCAG
    G  S  I  N  H  N  A  Y  N  P  S  M  E  T  D  F  V  P  E  Q

781 ACAGCACCTGACACAACAGTTTCACATCCAAAAACGCACAAAGGGAAGACAGCACAACTA
    T  A  P  D  T  T  V  S  H  P  K  T  H  K  G  K  T  A  Q  L

841 CCTGAACCTCTAATTCAGATTCTCAGTCCAATGGACAGAGAAGCTAGAGTCCTGAGATAC
    P  E  P  L  I  Q  I  L  S  P  M  D  R  E  A  R  V  L  R  Y

901 AGAGAGAAGAAGAAGAGAAGAAAGTTTGAGAAGACAATAAGGTATGCTTCAAGGAAGGCA
    R  E  K  K  K  R  R  K  F  E  K  T  I  R  Y  A  S  R  K  A

961 TATGCAGAGAGAAGACCGAGGATAAATGGACGGTTTGCAAAGATGAGTGAAACCGAAGTA
    Y  A  E  R  R  P  R  I  N  G  R  F  A  K  M  S  E  T  E  V

1021 GAGGACCAAGAGTACAACACAATGCTAATGTACTGCGACACAGGATATGGCATTGTTCCT
    E  D  Q  E  Y  N  T  M  L  M  Y  C  D  T  G  Y  G  I  V  P

1081 TCATTCTATGGCCAAAAATAA
    S  F  Y  G  Q  K  *
```

GENETIC CONTROL OF FLOWERING

FIELD OF THE INVENTION

This invention relates to the genetic control of flowering in plants and the cloning and expression of genes involved therein. More particularly, the invention relates to the cloning and expression of the CONSTANS (CO) gene of *Arabidopsis thaliana*, and homologues from other species, including *Brassica napus* and manipulation and use of the gene in plants.

Efficient flowering in plants is important, particularly when the intended product is the flower or the seed produced therefrom. One aspect of this is the timing of flowering: advancing or retarding the onset of flowering can be useful to farmers and seed producers. An understanding of the genetic mechanisms which influence flowering provides a means for altering the flowering characteristics of the target plant. Species for which flowering is important to crop production are numerous, essentially all crops which are grown from seed, with important examples being the cereals, rice and maize, probably the most agronomically important in warmer climatic zones, and wheat, barley, oats and rye in more temperate climates. Important seed products are oil seed rape and canola, sugar beet, maize, sunflower, soyabean and sorghum. Many crops which are harvested for their roots are, of course, grown annually from seed and the production of seed of any kind is very dependent upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

*Arabidopsis thaliana* is a facultative long day plant, flowering early under long days and late under short days. Because it has a small, well-characterized genome, is relatively easily transformed and regenerated and has a rapid growing cycle, Arabidopsis is an ideal model plant in which to study flowering and its control.

We have discovered that one of the genes required for this response to photoperiod is the CONSTANS or CO gene, also called FG. We have found that plants carrying mutations of this gene flower later than their wild-types under long days but at the same time under short days, and we conclude, therefore, that the CO gene product is involved in the promotion of flowering under long days.

Putterill et al, *Mol. Gen. Genet.* 239: 145–157 (1993) describes preliminary cloning work which involved chromosome walking with yeast artificial chromosome (YAC) libraries and isolation of 1700 kb of contiguous DNA on chromosome 5 of Arabidopsis, including a 300 kb region containing the gene CO. That work fell short of cloning and identification of the CO gene.

We have now cloned and sequenced the CO gene (Putterill et al., 1995), which is provided herein. Unexpected difficulties and complications were encountered which made the cloning harder than anticipated, as is discussed below in the experimental section.

SUMMARY OF THE INVENTION

According to a first aspect of the present invention there is provided a nucleic acid molecule comprising a nucleotide sequence encoding a polypeptide with CO function. Those skilled in the art will appreciate that "CO function" may be used to refer to the ability to influence the timing of flowering phenotypically like the CO gene of *Arabidopsis thaliana* (the timing being substantially unaffected by vernalisation), especially the ability to complement a co mutation in *Arabidopsis thaliana*, or the co phenotype in another species. CO mutants exhibit delayed flowering under long days, the timing of flowering being substantially unaffected by vernalisation (see, for example, Korneef et al. (1991)).

Nucleic acid according to the present invention may have the sequence of a CO gene of *Arabidopsis thaliana*, or be a mutant, derivative or allele of the sequence provided. Preferred mutants, derivatives and alleles are those which encode a protein which retains a functional characteristic of the protein encoded by the wild-type gene, especially the ability to promote flowering as discussed herein. Other preferred mutants, derivatives and alleles encode a protein which delays flowering compared to wild-type or a gene with the sequence provided. Changes to a sequence, to produce a mutant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence are included.

A preferred nucleic acid sequence for a CO gene is shown in FIG. 1 (SEQ ID NO:1), along with the encoded amino acid sequence of a polypeptide which has CO function.

The present invention also provides a vector which comprises nucleic acid with any one of the provided sequences, preferably a vector from which polypeptide encoded by the nucleic acid sequence can be expressed. The vector is preferably suitable for transformation into a plant cell. The invention further encompasses a host cell transformed with such a vector, especially a plant cell. Thus, a host cell, such as a plant cell, comprising nucleic acid according to the present invention is provided. Within the cell, the nucleic acid may be incorporated within the chromosome. There may be more than one heterologous nucleotide sequence per haploid genome. This, for example, enables increased expression of the gene product compared with endogenous levels, as discussed below.

A vector comprising nucleic acid according to the present invention need not include a promoter or other regulatory sequence, particularly if the vector is to be used to introduce the nucleic acid into cells for recombination into the genome.

Nucleic acid molecules and vectors according to the present invention may be provided isolated from their natural environment, in substantially pure or homogeneous form, or free or substantially free of nucleic acid or genes of the species of interest or origin other than the sequence encoding a polypeptide able to influence flowering, eg in *Arabidopsis thaliana* nucleic acid other than the CO sequence.

Nucleic acid may of course be double- or single-stranded, cDNA or genomic DNA, RNA, wholly or partially synthetic, as appropriate.

The present invention also encompasses the expression product of any of the nucleic acid sequences disclosed and methods of making the expression product by expression from encoding nucleic acid therefore under suitable conditions in suitable host cells. Those skilled in the art are well able to construct vectors and design protocols for expression and recovery of products of recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example *Molecular Cloning: a Laboratory Manual:* 2nd edition, Sambrook et al, 1989, Cold Spring Harbor Laboratory Press. Transformation procedures depend on the host used, but are well known.

The present invention further encompasses a plant comprising a plant cell comprising nucleic acid according to the present invention, and selfed or hybrid progeny and any descendant of such a plant, also any part or propagule of such a plant, progeny or descendant, including seed.

A further aspect of the present invention provides a method of identifying and cloning CO homologues from plant species other than *Arabidopsis thaliana* which method employs a nucleotide sequence derived from that shown in FIG. 1 (SEQ ID NO:1). The genes whose sequences are shown in FIG. 5 (SEQ ID NO:5) and FIG. 6 (SEQ ID NO:7) were cloned in this way. Sequences derived from these may themselves be used in identifying and in cloning other sequences. The nucleotide sequence information provided herein, or any part thereof, may be used in a data-base search to find homologous sequences, expression products of which can be tested for ability to influence a flowering characteristic. These may have "CO function" or the ability to complement a mutant phenotype, which phenotype is delayed flowering (especially under long days), preferably the timing of flowering being substantially unaffected by vernalisation, as disclosed herein. Alternatively, nucleic acid libraries may be screened using techniques well known to those skilled in the art and homologous sequences thereby identified then tested.

The present invention also extends to nucleic acid encoding a CO homologue obtained using a nucleotide sequence derived from that shown in FIG. 1 (SEQ ID NO:1). CO homologue sequences are shown in FIGS. 5 (SEQ ID NO:5) and 6 (SEQ ID NO:7). Also encompassed by the invention is nucleic acid encoding a CO homologue obtained using a nucleotide sequence derived from a sequence shown in FIG. 5 (SEQ ID NO:5) or FIG. 6 (SEQ ID NO:7).

The CO protein contains an arrangement of cysteines at the amino end of the protein that is characteristic of zinc fingers, such as those contained within the GATA transcription factors (discussed by Ramain et al, 1993; S ánchez-Garciá and Rabbitts, 1994). Seven independently isolated co mutants have been described, and we have identified the sequence changes causing a reduction in CO activity in all seven cases. Five of them have alterations within regions proposed from their sequence to form zinc fingers, and the other two have changes in adjacent amino acids at the carboxy terminus of the protein. The positions of these alterations support our interpretation that CO encodes a protein containing zinc fingers that probably binds DNA and acts as a transcription factor.

The provision of sequence information for the CO gene of *Arabidopsis thaliana* enables the obtention of homologous sequences from other plant species. In Southern hybridization experiments a probe containing the CO gene of *Arabidopsis thaliana* hybridises to DNA extracted from *Brassica nigra, Brassica napus* and *Brassica oleraceae*. Different varieties of these species display restriction fragment length polymorphisms when their DNA is cleaved with a restriction enzyme and hybridised to a CO probe. These RFLPs may then be used to map the CO gene relative to other RFLPs of known position. In this way for example, three CO gene homologues were mapped to linkage groups N5, N2 and N12 of *Brassica napus* (D. Lydiate, unpublished). The populations used for RFLP mapping had previously been scored for flowering time and it was demonstrated that particular alleles of the CO homologues segregated together with allelic variations affecting flowering time. The loci mapped to linkage groups N2 and N12 showed the most extreme allelic variation for flowering time.

Successful cloning of two *Brassica napus* homologues is described in Example 5.

This confirms that genes homologous to the CO gene of Arabidopsis regulate flowering time in other plant species.

Thus, included within the scope of the present invention are nucleic acid molecules which encode amino acid sequences which are homologues of CO of *Arabidopsis thaliana*. Homology may be at the nucleotide sequence and/or amino acid sequence level. Preferably, the nucleic acid sequence shares homology with the sequence encoded by the nucleotide sequence of FIG. 1 (SEQ ID NO:1), preferably at least about 50%, or 60%, or 70%, or 80% homology, most preferably at least 90% homology, from species other than *Arabidopsis thaliana* and the encoded polypeptide shares a phenotype with the *Arabidopsis thaliana* CO gene, preferably the ability to influence timing of flowering. These may promote or delay flowering compared with *Arabidopsis thaliana* CO and mutants, derivatives or alleles may promote or delay flowering compared with wild-type.

CO gene homologues may also be identified from economically important monocotyledonous crop plants such as rice and maize. Although gene encoding the same protein in monocotyledonous and dicotyledonous plants show relatively little homology at the nucleotide level, amino acid sequences are conserved. In public sequence databases we recently identified several Arabidopsis cDNA clone sequences that were obtained in random sequencing programmes and share homology with CO in regions of the protein that are known to be important for its activity. Similarly, among randomly sequenced rice cDNAs we identified one clone that shared relatively little homology to CO at the DNA level but showed high homology at the amino acid level. This clone, and another one that we have identified from maize, may be used to to identify the whole CO gene family from rice and other cereals. By sequencing each of these clones, studying their expression patterns and examining the effect of altering their expression, genes carrying out a similar function to CO in regulating flowering time are obtainable. Of course, mutants derivatives and alleles of these sequences are included within the scope of the present invention in the same terms as discussed above for the *Arabidopsis thaliana* CO gene.

Nucleic acid according to the invention may comprise a nucleotide sequence encoding a polypeptide able to complement a mutant phenotype which is delayed flowering, the timing of flowering being substantially unaffected by vernalisation. The delay flowering may be under long days. Also the present invention provides nucleic acid comprising a nucleotide sequence which is a mutant or derivative of a wild-type gene encoding a polypeptide with ability to influence the timing of flowering, the mutant or derivative phenotype being early or delayed flowering with the timing of flowering being substantially unaffected by vernalisation. These are distinguished from the LD gene reported by Lee et al.

Vernalisation is low-temperature (usually just above 0° C.) treatment of plant (seedlings) or seed for a period of usually a few weeks, probably about 30 days. It is a treatment required by some plant species before they will break bud or flower, simulating the effect of winter cold.

Also according to the invention there is provided a plant cell having incorporated into its genome a sequence of nucleotides as provided by the present invention, under operative control of a regulatory sequence for control of expression. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

Plants which comprise a plant cell according to the invention are also provided, along with any part or propagule thereof, seed, selfed or hybrid progeny and descendants.

The invention further provides a method of influencing the flowering characteristics of a plant comprising expression of a heterologous CO gene sequence (or mutant, allele, derivative or homologue thereof, as discussed) within cells of the plant. The term "heterologous" indicates that the gene/sequence of nucleotides in question have been introduced into said cells of the plant using genetic engineering, ie by human intervention. The gene may be on an extra-genomic vector or incorporated, preferably stably, into the genome. The heterologous gene may replace an endogenous equivalent gene, ie one which normally performs the same or a similar function in control of flowering, or the inserted sequence may be additional to the endogenous gene. An advantage of introduction of a heterologous gene is the ability to place expression of the gene under the control of a promoter of choice, in order to be able to influence gene expression, and therefore flowering, according to preference. Furthermore, mutants and derivatives of the wild-type gene, eg with higher or lower activity than wild-type, may be used in place of the endogenous gene.

The principal flowering characteristic which may be altered using the present invention is the timing of flowering. Under-expression of the gene product of the CO gene leads to delayed flowering (as suggested by the co mutant phenotype); over-expression may lead to precocious flowering (as demonstrated with transgenic Arabidopsis plants carrying extra copies of the CO gene and by expression from CaMV 35S promoter). This degree of control is useful to ensure synchronous flowering of male and female parent lines in hybrid production, for example. Another use is to advance or retard the flowering in accordance with the dictates of the climate so as to extend or reduce the growing season. This may involve use of anti-sense or sense regulation.

A second flowering characteristic that may be altered is the distribution of flowers on the shoot. In Arabidopsis, flowers develop on the sides but not at the apex of the shoot. This is determined by the location of expression of the LEAFY genes (Weigel et al., 1992), and mutations such as terminal flower (Shannon and Meeks-Wagner, 1991) that cause LEAFY to be expressed in the apex of the shoot also lead to flowers developing at the apex. There is evidence that CO is required for full activity of LEAFY (Putterill et al., 1995), and therefore by increasing or altering the pattern of CO expression the level and positions of LEAFY expression, and therefore of flower development, may also be altered. This is exemplified in Example 4. This may be employed advantageously in creating new varieties of horticultural species with altered arrangements of flowers.

The nucleic acid according to the invention, such as a CO gene or homologue, may be placed under the control of an externally inducible gene promoter to place the timing of flowering under the control of the user. The use of an inducible promoter is described below. This is advantageous in that flower production, and subsequent events such as seed set, may be timed to meet market demands, for example, in cut flowers or decorative flowering pot plants. Delaying flowering in pot plants is advantageous to lengthen the period available for transport of the product from the producer to the point of sale and lengthening of the flowering period is an obvious advantage to the purchaser.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level invirtually all plant tissues (Benfey et al, 1990a and 1990b); the maize gluthathione-S-transferase isoform II (GST-II-27) gene promoter which is activated in response to application of exogenous safener (WO93/01294, ICI Ltd); the cauliflower meri 5 promoter that is expressed in the vegetative apical meristem as well as several well localised positions in the plant body, eg inner phloem, flower primordia, branching points in root and shoot (Medford, 1992; Medfore et al, 1991) and the *Arabidopsis thaliana* LEAFY promoter that is expressed very early in flower development (Weigel et al, 1992).

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with a DNA segment containing the sequence may be produced by standard techniques for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966), electroporation (EP 290395, WO8706614) or other forms of direct DNA uptake (DE 4005152, WO9012096, U.S. Pat.

No. 4,684,611). Agrobacterium transformation is widely used by those skilled in the art to transform dicotyledonous species. Although Agrobacterium has been reported to be able to transform foreign DNA into some monocotyledonous species (WO 92/14828), microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

In the present invention, over-expression may be achieved by introduction of the nucleotide sequence in a sense orientation. Thus, the present invention provides a method of influencing a flowering characteristic of a plant, the method comprising causing or allowing expression of the polypeptide encoded by the nucleotide sequence of nucleic acid according to the invention from that nucleic acid within cells of the plant. (See Example 4.)

Under-expression of the gene product polypeptide may be achieved using anti-sense technology or "sense regulation". The use of anti-sense genes or partial gene sequences to down-regulate gene expression is now well-established. DNA is placed under the control of a promoter such that transcription of the "anti-sense" strand of the DNA yields RNA which is complementary to normal mRNA transcribed from the "sense" strand of the target gene. For double-stranded DNA this is achieved by placing a coding sequence or a fragment thereof in a "reverse orientation" under the control of a promoter. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works. See, for example, Rothstein et al, 1987; Smith et al, 1988; Zhang et al, 1992.

Thus, the present invention also provides a method of influencing a flowering characteristic of a plant, the method comprising causing or allowing anti-sense transcription from nucleic acid according to the invention within cells of the plant.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol, 1990; Napoli et al, 1990; Zhang et al, 1992.

Thus, the present invention also provides a method of influencing a flowering characteristic of a plant, the method comprising causing or allowing expression from nucleic acid according to the invention within cells of the plant. This may be used to suppress activity of a polypeptide with ability to influence a flowering characteristic. Here the activity of the polypeptide is preferably suppressed as a result of under-expression within the plant cells.

As stated above, the expression pattern of the CO gene may be altered by fusing it to a foreign promoter. For example, International patent application WO93/01294 of Imperial Chemical Industries Limited describes a chemically inducible gene promoter sequence isolated from a 27 kD subunit of the maize glutathione-S-transferase, isoform II gene (GST-II-27) (See FIG. 2 (SEQ ID NO:3)). It has been found that when linked to an exogenous gene and introduced into a plant by transformation, the GST-II-27 promoter provides a means for the external regulation of the expression of that exogenous gene. The structural region of the CO gene is fused to the GST-II-27 promoter downstream of the translation start point shown in FIG. 2 (SEQ ID NO:3).

The GST-II-27 gene promoter has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

Accordingly, the present invention provides in a further aspect a gene construct comprising an inducible promoter operatively linked to a nucleotide sequence provided by the present invention, such as the CO gene of *Arabidopsis thaliana*, a homologue from another plant species or any mutant, derivative or allele thereof. This enables control of expression of the gene. The invention also provides plants transformed with said gene construct and methods comprising introduction of such a construct into a plant cell and/or induction of expression of a construct within a plant cell, by application of a suitable stimulus, an effective exogenous inducer. The promoter may be the GST-II-27 gene promoter or any other inducible plant promoter.

Promotion of CO Activity to Cause Early Flowering

Mutations that reduce CO activity cause late flowering under inductive long day conditions, indicating CO involvement in promoting flowering under long days. It is probably not required under non-inductive short days because co mutations have no effect on flowering time under these conditions. The CO transcript is present at very low abundance under long days and has only been detected by using PCR to amplify cDNA. The observation that some transgenic plants harbouring a T-DNA containing CO flowered slightly earlier than wild type under long days and considerably earlier than wild type under short days, suggests that, particularly under non-inductive short days, the level of the CO transcript is limiting on flowering time. This suggests that flowering could be manipulated by using foreign promoters to alter the expression of the gene:

Causing Early Flowering Under Non-Inductive Conditions

Manipulation of CO transcript levels under non-inductive conditions may lead to early, or regulated, flowering. Promoter fusions such as those disclosed herein enable expression of CO mRNA at a higher level than that found in wild-type plants under non-inductive conditions. Use of CaMV35S or meri 5 fusions leads to early flowering while use of GSTII fusions leads to regulated flowering.

Causing Early Flowering Under Inductive Conditions

Wild-type Arabidopsis plants flower extremely quickly under inductive conditions and the CO gene is expressed prior to flowering, although at a low level. Nevertheless, some transgenic wild-type plants containing extra copies of CO have been shown to flower slightly earlier than wild-type plants. The level of the CO product may be increased by introduction of promoter, eg CaMV35S or meri 5, fusions. Inducible promoters, such as GSTII, may be used to regulate flowering, eg by first creating a CO mutant of a particular species and then introducing an inducible promoter-CO fusion capable of complementation of the mutation in a regulated fashion.

Inhibition of CO Activity to Cause Late Flowering co mutations cause later flowering of Arabidopsis. Transgenic approaches may be used to reduce Co activity and thereby delay or prevent flowering in a range of plant species. A variety of strategies may be employed.

Expression of Sense or Anti-Sense RNAs

In several cases the activity of endogenous plant genes has been reduced by the expression of homologous antisense RNA from a transgene, as discussed above. Similarly, the expression of sense transcripts from a transgene may reduce the activity of the corresponding endogenous copy of the gene, as discussed above. Expression of a CO antisense or sense RNA should reduce activity of the endogenous gene and cause late flowering.

Expression of Modified Versions of the CO Protein

Transcription factors and other DNA binding proteins often have a modular structure in which amino acid sequences required for DNA binding, dimerisation or transcriptional activation are encoded by separate domains of the protein (Reviewed by Ptashne and Gann, 1990). This permits the construction of truncated or fusion proteins that display only one of the functions of the DNA binding protein. In the case of CO, modification of the gene in vitro and expression of modified versions of the protein may lead to dominant inhibition of the endogenous, intact protein and thereby delay flowering. This may be accomplished in various ways, including the following:

Expression of a Truncated CO Protein Encoding only the DNA Binding Region

The zinc-finger containing region of CO may be required and sufficient to permit binding to DNA. If a truncated or mutated protein that only encodes the DNA binding region were expressed at a higher level than the endogenous protein, then most of the CO binding sites should be occupied by the mutated version thereby preventing binding of the fully active endogenous protein. Binding of the mutant protein would have the effect of preventing CO action, because the mutated protein would not contain any other regions of CO that might be involved in biological processes such as transcriptional activation, transcriptional inhibition or protein-protein interaction.

In vitro analysis of a murine transcription factor GF1 that contains zinc-fingers similar to those of CO, suggests that a truncated CO protein with the properties described above could be designed. Martin and Orkin (1990) demonstrated that a truncated version of GF1 containing only the zinc fingers retained DNA binding activity, but was incapable of transcriptional activation. Similarly, the zinc-finger containing PANNIER protein of *Drosophila melanogaster* is required to repress activation of genes required for bristle formation. Mutations in a domain that does not contain the zinc fingers caused dominant super-repression of gene activity, probably because these proteins bind DNA but no not interact with other proteins in the way that the wild-type protein does (Ramain et al, 1993).

Expression of a Mutant CO Protein Not Encoding the DNA Binding Domain

A second form of inhibitory molecule may be designed if CO must dimerise, or form complexes with other proteins, to have its biological effect, and if these complexes can form without a requirement for CO being bound to DNA. In this case expression of a CO protein that is mutated within the DNA-binding domain, but contains all of the other properties of the wild-type protein, would have an inhibitory effect. If the mutant protein were present at a higher concentration than the endogenous protein and CO normally forms dimers, then most of the endogenous protein would form dimers with the mutant protein and would participate in the majority of these complexes which would not bind DNA. Similarly, if CO forms complexes with other proteins, then the mutant form of CO would then not bind DNA.

Mutant forms of DNA-binding proteins with these properties have been reported previously. For example, in yeast cells expression of a protein containing the transcriptional activation domain of GAL4 was able to reduce the expression of the CYC1 gene. CYC1 is not normally activated by GAL4, so it was proposed that the GAL4 activating domain sequesters proteins required for CYC1 activation (Glll and Ptashne, 1988). Similarly, mutations in the zinc finger region of the PANNIER protein of *Drosophila melanogaster* have a dominant phenotype, probably because the mutant proteins sequester proteins essential for PANNIER activity and reduce their availability to interact with wild-type protein (Ramain, 1993)

Aspects and embodiments of the present invention will now be illustrated, by way of example, with reference to the accompanying figures. Further aspects and embodiments will be apparent to those skilled in the art. All documents mentioned in this text are incorporated herein by reference.

FIG. 1 shows a nucleotide sequence according to one embodiment of the invention, being the sequence of the CO ORF obtained from *Arabidopsis thaliana* (SEQ ID NO. 1), and the predicted amino acid sequence (SEQ ID NO. 2). The nucleotide sequence is shown above the amino acid sequence. The region shown in bold is thought to encompass both zinc finger domains.

FIGS. 2A and 2B show the nucleotide sequence of the GST-II-27 gene promoter (SEQ ID NO. 3). The fragment used to make the fusion was flanked by the HindIII and NdeI sites that are shown in bold.

FIGS. 3A–3C show the nucleotide sequence of the genomic DNA comprising the CO gene obtained from *Arabidopsis thaliana,* including the single intron, promoter sequences and sequences present after the translational termination codon (SEQ ID NO. 4). The genomic region shown starts 2674 bp upstream of the translational start site, and ends just after the polyadenylation site. The CO open reading frame is shown in bold, and is interrupted by the single intron.

FIG. 5 shows a nucleotide sequence according to a further embodiment of the invention, being a CO ORF obtained from *Brassica napus* (SEQ ID NO. 5), and the predicted amino acid sequence (SEQ ID NO. 6).

FIG. 6 shows a nucleotide sequence according to a further embodiment of the invention, being a second CO ORF obtained from *Brassica napus* (SEQ ID NO. 7), and the predicted amino acid sequence (SEQ ID NO. 8).

DETAILED DESCRIPTION OF THE INVENTION

EXAMPLE 1

Figure 4:
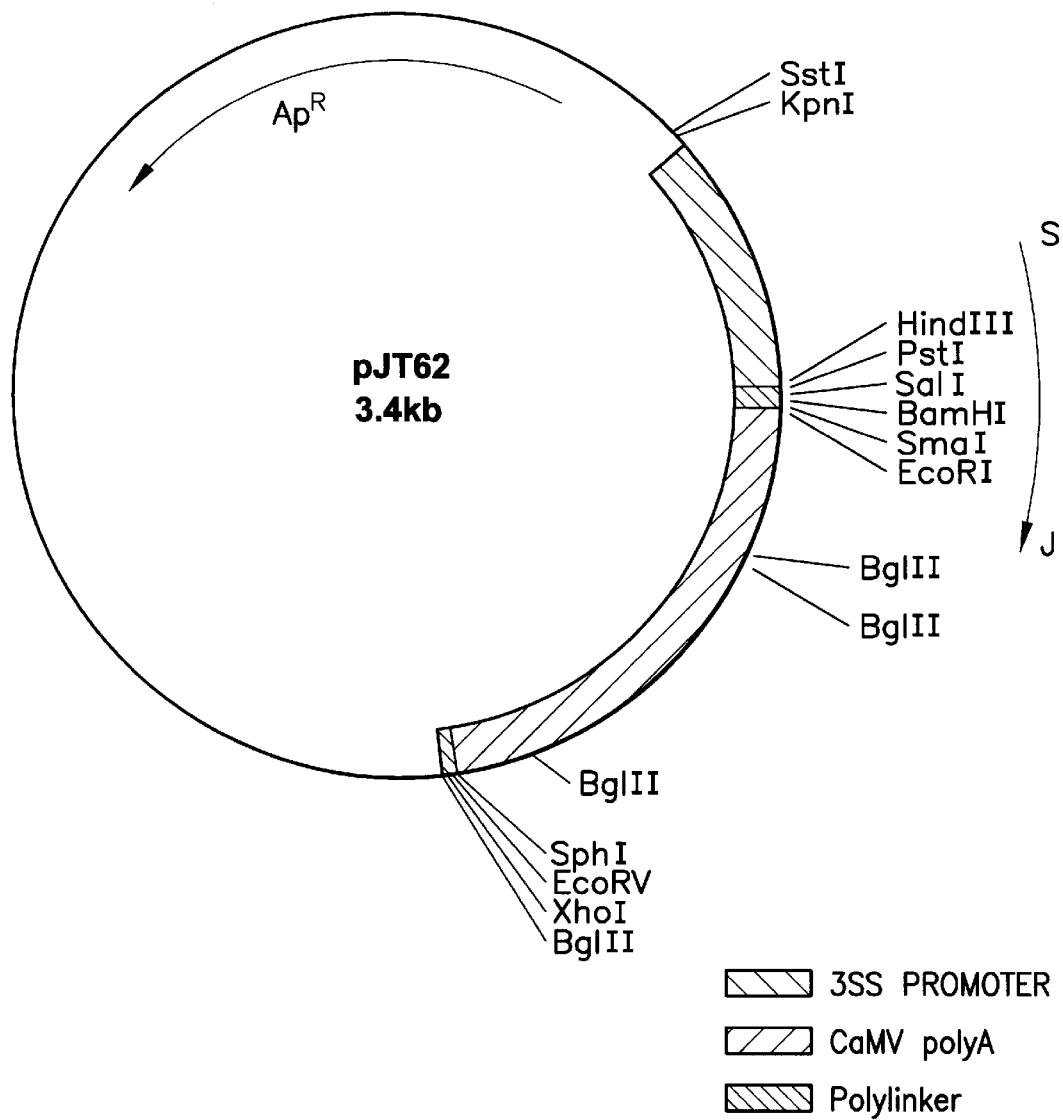
FIG. 4 shows the pJIT62 plasmid used as a source of the CaMV 355 promoter. The KpnI-HindIII fragment, shown as a dark coloured thick line, was used as a source of the promoter.

Cloning and Analysis of a CO Gene Cosmid and RFLP Markers

DNA of λ CHS2 was obtained from R. Feinbaum (Massachusetts General Hospital (MGH), Boston). Total DNA was used as radiolabelled probe to YAC library colony filters and plant genomic DNA blots. Cosmids g6833, 17085, 17861, 19027, 16431, 14534, g5962 and g4568 were obtained from Brian Hauge (MGH, Boston), cultured in the presence of 30 µg/ml kanamycin, and maintained as glycerol stocks at −70° C. Total cosmid DNA was used as radiolabelled probe to YAC library colony filters and plant genomic DNA blots. Cosmid pCIT1243 was provided by Elliot Meyerowitz (Caltech, Pasadena), cultured in the presence of 100 µg/ml streptomycin/spectinomycin and maintained as a glycerol stock at −70° C. pCIT30 vector sequences share homology to pYAC4 derived vectors, and therefore YAC library colony filters were hydridised with insert DNA extracted from the cosmid. Total DNA of pCIT1243 was used as radiolabelled probe to plant genomic DNA blots.

YAC libraries.

The EG, abi and S libraries were obtained from Chris Somerville (Michigan State University). The EW library was obtained from Jeff Dangl (Max Delbrück Laboratory, Cologne) and the Yup library from Joe Ecker (University of Pennsylvania). Master copies of the libraries were stored at −70° C. (as described by Schmidt et al. Aust. J. Plant Physiol. 19: 341–351 (1992)). The working stocks were maintained on selective *Kiwebrew agar* at 4° C. Kiwibrew is a selective, complete minimal medium minus uracil, and containing 11% Casamino acids. Working stocks of the libraries were replated using a 96-prong replicator every 3 months.

Yeast colony filters.

Hybond-N (Amersham) filters (8 cm×11 cm) containing arrays of yeast colony DNA from 8–24 library plates were produced and processed (as described by Coulson et al. Nature 335:184–186 (1988) and modified (as described by Schmidt and Dean Genome Analysis, vol.4: 71–98 (1992)). Hydridisation and washing conditions were according to the manufacturer's instrucxtions. Radiolabelled probe DNA was prepared by random-hexamer labelling.

Yeast chromosome preparation and fractionation by pulsed field gel electrophoresis (PFGE).

Five milliliters of Kiwibrew was incoculated with a single yeast colony and cultured at 30° C. for 24 h. Yeast spheroplasts were generated by incubation with 2.5 mg/ml Novozym (Novo Biolabs) for 1 h at room temperature. Then 1 M sorbitol was added to bring the final volume of spheroplasts to 50 µl. Eighty microliters of molten LMP agarose (1% InCert agarose, FMC) in 1 M sorbitol was added to the spheroplasts, the mixture was vortexed briefly and pipetted into plug moulds. Plugs were placed into 1.5 ml Eppendorf tubes and then incubated in 1 ml of 1 mg/ml Proteinase K (Boehringer Mannheim) in 100 mMEDTA, pH 8, 1% Sarkosyl for 4 h at 50° C. The solution was replaced and the plugs incubated overnight. The plugs were washed three times for 30 min each with TE and twice for 30 min with 0.5×TVBE. PFGE was carried out using the Pulsaphor system (LKB). One-third of a plug was loaded onto a 1% agarose gel and electrophoresed in 0.5×TBE at 170 V, 20 s pulse time, for 36 h at 4° C. DNA markers were concatemers of λ DNA prepared as described by Bancroft and Wolk, Nucleic A Res. 16:7405–7418 (1998). DNA was visualised by staining with ethidium bromide.

Yeast genomic DNA for restriction enzyme digestion and inverse polymerase chain rection (IPCR).

Yeast genomic DNA was prepared essentially as described by Heard et al. (1989) except that yeast spheroplasts were prepared as above. Finally, the DNA was extracted twice with phenol/chloroform, once with chloroform and ethanol precipitated. The yield from a 5 ml culture was about 10 µg DNA.

Isolation of YAC end fragments by IPCR.

Yeast genomic DNA (100 ng) was digested with AluI, HaeIII, EcoRV or HindII. The digestions were phenol-chloroform extracted once and then ethanol precipitated. The DNA fragments were circularised by ligation in a volume of 100 µl over-night at 16° C. in the presence of 2 U ligase (BRL). After incubation of the ligation mixture at 65° C. for 10 min, IPCR was carried out on 10 µl ligation mixture using inverse primer pairs. The IPCR conditions and C and D primer pairs have been described by Schmidt et al. (1992). The JP series are from M. Hirst (IMM Molecular Genetics Group, Oxford).

After digestion with the indicated enzymes, the following primer pairs were used:

For left-end IPCR:

AluI, EcoRV; D71 (SEQ ID NO:9) 5'tcctgctcgcttcgctactt3' and C78 (SEQ ID NO:10) 5'-gcgatgctgtcggaatggac3'

HaeIII; JP1 (SEQ ID NO:11) 5'aagtactctcggtagccaag3' and JP5 (SEQ ID NO:12) 5'-gtgtggtcgccatgatcgcg3'.

For right-end IPCR:

AluI, HincII; C69 (SEQ ID NO:13) 5'ctgggaagtgaatg-gagacata3' and C70 (SEQ ID NO:14) 5'aggagtcgcat-aagggagag3'

HaeIII; C69 and JP4 (SEQ ID NO: 31) 5'ttcaagctctacgc-cgga3'.

Aliquots of the IPCR reactions were checked by electrophoresis on a 1.5% agarose gel and the 1 µl of the reaction was re-amplified by PCR using the conditions and F primer series recommended by I. Hwang (MGH, Boston). Conditions for re-amplification were the same as for IPCR, except that 30 cycles (1 min, 94° C.; 1 min, 45°° C.; and 3 min, 72° C.) were used. The F primers anneal very near the cloning site and so reduce the amount of vector sequence present in the PCR product. In addition they introduce a FokI site very close to the destroyed cloning site of EW and S YACs.

The primers used for re-amplification of left-end IPCR products were as follows:

For EG, abi and S YACs:

AluI, F2 (SEQ ID NO:15) 5'acgtcggatgctcactatagggatc3' and C77 (SEQ ID NO:16) 5'gtgataaactaccgcattaaagc3';

HaeIII, F2 and JP5; EcoRV, F2 and 78.

For EW and Yup YACs; AluI,

F6 (SEQ ID NO:17) 5'acgtcggatgactttaatttattcacta3' and C77; HaeIII, F6 and JP5; EcoRV, F6 and C78.

The following primers were used for re-amplification of the right-end IPCR products:

For EG, abi and S YACs: AluI,

F3 (SEQ ID NO:18) 5'gacgtggatgctcactaaagggatc3' and C71 (SEQ ID NO:19) 5'agagccttcaacccagtcag3';

HaeIII, F3 and JP4; HincII, F3 and C70.

For EW and YUP YACs: AluI,
F7 (SEQ ID NO:20) 5'acgtcggatgccgatctcaagatta3' and C77; HaeIII, F7 and J94; 4HincII, F7 and C70.

The resulting PCR product was purified by cleaving with the enzyme originally used in the digestion together with BamHI (EG and abi YACs) or EcoRI (Yup YACs) and separated on 1% LMP agarose gels. The YAC end probes were radiolabelled using random priming in molten agarose, and in appropriate cases digested with FokI to remove vector sequences and then used as hydridisation probes.

Isolation of YAC left-end probes by plasmid rescue.

Plasmid rescue of YAC left-end fragments from EG, abi and EW YACs was carried out as described by Schmidt et al. (1992).

Isolation of plant genomic DNA.

Plant genomic DNA was isolated from glasshouse grown plants essentially as described by Tai and Tanksley, Plant Mol. Biol. Rep. 8: 297–303 (1991), except that the tissue was ground in liquid nitrogen and the RNase step omitted. Large-scale (2.5–5 g leaves) and miniprep (3–4 leaves) DNA was prepared using this method.

Gel blotting and hydridisation conditions.

Gel transfer to Hybond-N, hybridisation and washing conditions were according to the manufacturer's instructions, except that DNA was fixed to the filters by UV Stratalinker treatment (1200 μJ×100; Stratagene) and/or baked at 80° C. for 2 h. Radiolabelled DNA was prepared by random hexamer labelling.

RFLP analysis.

Two to three micrograms of plant genomic DNA was prepared from the parental plants used in the crosses and cleaved in a 300 μl volume with 1 of 17 restriction enzymes: DraI, BclI, CfoI, EcoRI, EcoRV, HincII, BglIII, RsaI, BamHI, HindIII, SacI, AluI, HinfI, Sau3A, TaqI and MboI. The digested DNA was ethanol precipitated and separated on 0.7% agarose gels and blotted onto Hybond-N filters. Radiolabelled cosmid λ or YAC end probe DNA was hybridised to the filters to identify RFLPs.

Selection of plants carrying recombination events in the vicinity of co.

The first sep in selecting recombinants was to create lines carrying the co mutation and closely linked markers. This was done twice for different flanking markers. In the first experiment a Landsberg erecta line carrying the co-2 allele (Koornneef et al. 1991) and tt4 was made. The tt4 mutation prevents the production of anthocyanin and has previously been suggested to be a lesion in the gene encoding chalcone synthase, because this map to a similar location (Chang et al. 1988). The double mutant was crossed to an individual of the Niederzenz ecotype and the resulting hybrid self-fertilised to produce an $F_2$ population. This population was then screened phenotypically for individuals in which recombination had occurred between co-2 and tt4. In addition, $F_2$ plants homozygous for both mutations were used to locate marker RFLP g4568 relative to co-2.

The second experiment was performed by using two marked lines as parents. The first of these contained chp7 in a Landsberg erecta background and was derived by Maarten Koorneef (Wageningen) from a cross between a line of undefined background (obtained from George Rédei) to Landsberg erecta. The second parent contained markers lu and Alb2. This was selected by Maarten Koorneef from a cross of a plant of S96 background carrying the alb2 mutation (M4-6-18; Relichová 1976) to a line containing co-1 and lu (obtained by Koorneef from J. Relichová, but originally from Cr. Rédei). The chp7, co-1 line was then crossed to the lu, alb2 line and an $F_2$ population derived by self-fertilisation of the hybrid. This population was used to isolate the recombinants with crossovers between lu and co-1 and between co-1 and alb2. Both classes of recombinants were recognised phenotypically as lu homozygotes. These are only present if recombination occurs between lu and alb2, because alb2 is lethal when homozygous.

Isolation of the CO (FG) locus:

The CO gene is located on the upper arm of chromosome 5 and is 2 cM proximal to tt4. The average physical distance in 1 cM in Arabidopsis is approximately 140 kb. The distance from CHS to CO might be expected therefore to be ca. 300 kb.

We started by hybridising 4 RFLP markers that are closely linked (within ca. 2 cM) to CHS to the EG and EW YAC libraries. This produced 18 hybridising YACs. These were run out on pulse field gels, Southern blotted and hybridised to the appropriate RFLP clone. This confirmed the colony hybridisation result and measured the size of the YACs; they ranged from 50 kb to 240 kb in size. The YACs were then digested with restriction enzymes, hybridised to RFLP marker DNA and the pattern of fragments compared to that of the marker. This allowed us to determine whether they contained all the fragments in the RFLP marker or only some of them and permitted us to deduce how the YACs lay in relation to each other. In most cases this arrangement was later confirmed by the isolation of inverse polymerise chain reaction (PCR) generated fragments which are located at the ends of the Arabidopsis DNA inserted with the YAC, and hybridisation of these to the appropriate overlapping YACs.

The short contigs around the RFLP markers were than extended. We obtained two sets of overlapping cosmid clones from this area and used the appropriate ones against the YAC libraries. This identified two new YACs. End probes derived from most of the 20 YACs we had identified were then used to screen the libraries and new YACs extending the cloned region in both directions were identified. In all a detailed analysis of 67 YACs was necessary. It allowed us to assemble one contiguous segment of Arabidopsis DNA which includes RFLP markers 6833, CHS, pCIT1243 and 5962 and is approximately 1700 kb long.

The location of CO within the contig was determined by detailed RFLP analysis after the isolation of recombinants containing cross-overs very closely linked to CO. The recombinants were identified by using flanking phenotypic markers. First we made a Landsberg erecta chromosome marked with co and tt4. Then we crossed this to Niedersenz and screened 1200 F2 plants for recombinant chromosomes carrying cross-overs between co and tt4. In this way we found twelve recombinants which were confirmed by scoring the phenotypes of their progeny. The rarity of these recombinants confirmed the extremely close linkage between tt4 and co. These recombinants were then used to locate CO on the contig. For example, some of them contain Landsberg DNA on the tt4 side of the cross-over and Niedersenz DNA on the co side. DNa isolated during our walk was positioned relative to CO by using small fragments as RFLP markers and hydridising them to the DNA extracted from the recombinants. We used a similar approach on the proximal side by screening for recombinants between co and alb2. This work initially located CO between two YAC end probes which are approximately 300 kb apart.

To locate CO more accurately within the 300 kb, more cross overs between co and the flanking phenotypic markers were screened for. Using a similar rationale as that described earlier, a total of 46 cross-overs between co and alb2 (an interval of 1.6 cM proximal to CO), and 135 between co and lu (an interval of 5.3 cM distal to CO) were identified and analysed with appropriate RFLP markers derived from our contig. This located the gene to a very short region defined by two YAC end probes. These were used to screen a cosmid library provided to us by University of Minnesota, and a short cosmid contig containing 3 cosmids that spanned the entire region was constructed. Analysis of these cosmids indicated that the detailed RFLP mapping had located CO to a region approximately 38 kb long.

To position the gene within the cosmids, each of them was introduced into co mutants and the resulting plants examined to determine which of the cosmids corrected the co mutant phenotype. Roots of plants homozygous for co-2 and tt4 mutations were co-cultivated with Agrobacterium strains containing each cosmid (Olszewski and Ausubel, 1988; Valvekens et al 1989) and kanamycin resistant plants regenerated. The regenerants (T1 generation) were self-fertilised and their progeny sown on medium containing kanamycin to confirm that they contained the T-DNA (Table 1).

A total of 5 independent transformants containing cosmid A, 9 containing cosmid B and 13 containing cosmid C produced kanamycin resistant T2 progeny and were studied further. The flowering time of 20–40 plants from each of these T2 families was measured in the long day greenhouse. All of the progeny of transgenic plants made with cosmid A flowered as late as the co-2 mutants, suggesting that this cosmid did not contain the CO gene. However, several of the families derived from plants containing cosmids B and C included early flowering individuals. In total, 6 of the 9 families derived from plants harboring cosmid B and 12 of the 13 derived from those carrying cosmid C contained plants that flowered as early as wild-type. All of these early-flowering individuals produced light coloured seeds indicating that they carried the tt4 mutation present in the line used for the transformation, and therefore were not simply the result of the experiment being contaminated with seeds of wild-type plants (Experimental Procedures). These results strongly suggest that the CO gene is contained in both cosmids B and C.

Further experiments were carried out in the T3 generation to confirm the complementation results. A total of five T2 early-flowering plants derived from cosmid B and six from cosmid C were self fertilised and studied further in the T3 generation. Each of the T2 plants chosen for this analysis was derived from a different transformant, was the earliest flowering plant in the T2 family and was a member of a family that had shown a ratio of 3 kanamycin resistant seedlings for each kanamycin sensitive, and therefore probably contained the transgene at only one locus (Table 1). All of the seedlings in these T3 families were resistant to kanamycin demonstrating that the parental T2 plants were homozygous for the T-DNA. This demonstrated that the earliest flowering T2 plants were homozygous for the CO transgene.

Under the long-day conditions used the co-2 mutant plants flowered considerably later than the wild-type controls (Table 1). The T3 plants flowered at least as early as wild-type under defined long-day conditions, and some individuals flowered earlier than wild-type (Table 1). This analysis confirmed that cosmids B and C can correct the effect of the co-2 mutation on flowering time under long days, suggesting that both of these cosmids contained CO, and therefore that the gene was in the region of overlap between them. This region was 6.5 kb long.

We determined the sequence of the 6.5 kb that was shared by cosmids B and C. This contains only one gene that we can readily identify from the DNA sequence. The polymerase chain reaction was used to amplify this gene from three independently isolated co mutants, and sequencing of these genes demonstrated that all three contained mutations. This, together with the complementation analysis, is conclusive evidence that this is the CO gene. The predicted amino acid sequence of CO shows no homology to previously reported genes. However, the amino terminus contains two regions that are predicted to form zinc fingers, suggesting that the protein product binds to DNA and is probably a transcription factor.

Unexpected difficulties in identifying CO within the 300 kb region defined by REG17B5 and LEW4A9

1. Locating the gene by more detailed RFLP mapping and complementation

As mentioned, Putterill et al. *Mol Gen. Genet.* 239:145–157 (1993) described location of CO to within a region of 300 kb. To locate CO more accurately by RFLP mapping, two materials were required: more recombinants carrying cross-overs within the 300 kb region, and more RFLP markers to use as probes against these recombinants.

Recombinants between lu and co or between co and alb2 were selected. A total of 68 cross-overs in the 1.6 cM between lu and co were identified, and 128 in the 5.3 cM between co and alb2. This is equivalent to 196 cross-overs in 6.8 cM, or an average of 29 cross-overs per cM. Among these recombinants, cross-overs within the 300 kb were unexpectedly under-represented: 300 kb is equivalent to around 1.5 cM, so 43 (29×1.5) cross-overs would be expected in this region. Only 23 were found.

The analysis of these cross-overs was also difficult because none of the YAC end probes that fell within the 300 kb could be used as RFLP probes. This was due to none of them detecting RFLPs between the parental lines used to make the recombinants. One RFLP marker (pCIT1243) was available within the region, and when this was used to analyse the recombinants it was found to be between REG17B5 and CO, thereby positioning the gene between pCIT1243 and LEW4A9. However, a more accurate position of the gene could not be achieved by this method because of the lack of suitable probes.

The distribution of cross-overs between pCIt1243 and LEW4A9 was asymmetric: there was one between pCIT1243 and CO and 19 between CO and LEW4A9. we guessed that the gene was likely to be close to pCIT1243. A pool of probes (LEG4C9, Labi19E1, pCIT1243, LEG21H11 and REG4C9) from this region was therefore used to screen a cosmid library to provide a series of cosmid clones extending from pCIT1243 towards LEW4A9. Analysis of these clones with individual probes showed that the three cosmids A, B and C extended from pCIT1243 in the direction required. These were then used as RFLP markers and the gene demonstrated to be on the cosmids.

The procedure was therefore more complex than that envisaged in the Putterill et al paper because of the difficulty in making enough recombinants within the 300 kb region, and in identifying suitable RFLP markers.

2. Identifying the gene by complementation

The three cosmids A, B and C were introduced into mutant plants, and it was shown that B and C could correct the effect of the mutation. The gene must therefore be on the DNA shared by B and C, but the method proposed in the Putterill paper for final identification of the CO gene failed. It had been assumed that one would be able to identify a transcript for CO by using the complementing DNA as a probe against Northern blots, or that one of the seven alleles would show a re-arrangement on Southern blots that would lead to the gene. In fact, we could not detect the CO transcript on Northern blots nor any re-arrangement indicative of where the gene might be.

The failure of this approach led us to sequence the genomic DNA that complemented the mutation. Computer analysis of this DNA identified two open reading frames adjacent to each other and we guessed that these might represent the CO gene. We still had no evidence that thes ORFs were actively transcribed, as one would expect for a gene, because no transcript was detectable on Northern blots and no cDNA was detected in several cDNA libraries. We therefore used the polymerase chain reaction (PCR) to amplify a cDNA from RNA preparations. This showed that these two ORFs did indeed represent one active gene. Sequencing co alleles then confirmed that they contained single base changes, or in one case a 9 bp deletion, that would not have been detected by the approaches proposed in the Putterill et al paper.

Gene Structure

To determine the gene structure, a cDNA for the CO gene was identified using RT-PCR (Experimental Procedures). The sequence of the cDNA contains an 1122 bp ORF that is derived from both ORFs identified in the genomic sequence by removal of a 233 bp intron. Translation of this open reading frame is predicted to form a protein containing 373 amino acids with a molecular mass of 42 kd. The transcription start site was not determined, but an in frame translation termination codon is located three codons upstream of the ATG, indicating that the entire translated region was identified. The 3' end of the transcript was located by sequencing four fragments produced by 3'-RACE. They all contained the poly-A tail at different positions with 5 bases of each other.

Available data bases were searched for proteins sharing homology with the predicted translation product of the CO gene. Searching the PROSITE directory detected no motifs within the CO protein. Moreover, a FASTA search comparing the CO protein sequence with those in GenBank detected no significant homologies. Direct comparison of the CO sequence with that of LUMINIDEPENDENS, the other flowering time gene cloned from Arabidopsis (Lee et al, 1994), detected no homology. However, analysis of the protein sequence by eye identified a striking arrangement of cysteine residues that is present in two regions near the amino terminus of the CO protein. Each of these regions contains four cysteines in $C-X_2-C-X_{16}-C-X_2-C$ arrangement, that is similar to the zinc-finger domains of GATA-1 transcription factors ($C-X_2-C-X_{17}-C-X_2-C$).

Comparison of two 43 amino acid stretches that are directly adjacent to each other within the predicted CO protein sequence and each of which contains one of the proposed zinc fingers, indicates striking homology; 46% of the amino acids are identical and 86% are either identical or related. The conservation is most apparent on the carboxy side of each finger, which is again reminiscent of GATA1 transcription factors, in which this region is a basic domain required for DNA binding and is highly conserved (Trainer et al, 1990; Brendel and Karlin, 1989; Ramain et al, 1993). In the CO protein this region is also positively charged; there is a net positive charge of 6 in the region adjacent to the amino finger and of 3 in the one next to the carboxy finger.

Comparison of the CO protein sequence of the CO zinc fingers with 116 amino acids that contain the zinc fingers of hGATA1 and are conserved between members of the GATA1 family (se Ramain et al, 1993) using the FASTA programme of the Wisconsin package identified one 81 amino acid region of homology that spans both zinc fingers of CO and aligns the cysteines of the zinc fingers of hGATA1 and those of CO. Between these regions of CO and hGATA1, twenty one percent of the amino acids are identical and 65% are similar or identical. Therefore although CO is not a member of the GATA1 family it shows similarity to them in the region of the zinc fingers and represents a new class of zinc-finger containing protein.

A further indication that these regions are important for CO activity is that the mutations in both the co-1 and co-2 alleles affect residues that are conserved between the proposed finger regions: co-2 changes an arginine on the carboxy side of the N-terminal finger to a histidine, and the co-1 deletion removes three amino acids from the carboxy side of the C-terminal finger.

Expression of CO mRNA in long and short day grown plants

No CO cDNA clones were found by screening several Arabidopsis cDNA libraries and the mRNA was not detected on Northern blots of polyA mRNA extracted from seedlings at the 3–4 leaf stage (data not shown). RT-PCR followed by Southern blotting and hybridisation to a CO specific probe was therefore used to detect the CO transcript. The RNA used in these experiments was isolated from seedlings at the 3–4 leaf stage, because this is just before the floral bud is visible under long days and therefore seemed a likely time for the gene to be expressed.

Six independent RNA preparations made from plants growing under long days all produced a hybridising fragment of the size expected for the CO cDNA. No difference in abundance of the CO transcript was detected between wild-type or co-1 mutant plants, suggesting that activity of the CO gene is not required to promote its own transcription. Flowering time under long days is influenced by CO gene dosage.

Plants that are heterozygous for a wild-type allele and either co-1 or co-2 flower at a time intermediate between co homozygotes and Landsberg erecta under long days (Koorneef et al, 1991; F. Robson, unpublished). Sequencing of these mutant alleles demonstrated that they both contain in frame alterations to the amino acid sequence. This might suggest two models for the partial dominance of co. The mutant alleles might give rise to an altered product that interferes with floral induction, or the mutations might cause loss of function and the two-fold reduction in the level of the CO protein in a heterozygote lead to a delay in flowering time (haplo-insufficiency). The haplo-insufficiency explanation is favoured by the results included herein.

In the complementation experiments, transgenic plants containing two copies of cosmids B or C and homozygous for the co-2 allele often flowered at the same time as wild-type plants under long days. If the mutant allele encoded a product that interfered with the activity of the wild-type protein, then this would not be expected to occur. Moreover, the need to use RT-PCR to detect the CO transcript suggests that it is present at very low levels, which is consistent with the possibility that further reductions in transcript level causes late flowering.

Increases in the dosage of CO can lead to slightly earlier flowering under long days. This was concluded from the observation that some of the transgenic lines carrying extra copies of the CO gene flowered slightly earlier than wild type plants (Tables 1 and 2). This observation, together with the haplo-insufficiency phenotype discussed above, suggests that the level of expression of CO is a critical determinant of flowering time of Arabidopsis under long days.

METHODS

Growth Conditions and Measurement of Flowering Time

Flowering time was measured under defined conditions by growing plants in Sanyo Gallenkamp Controlled Environment rooms at 20° C. Short days comprised a photoperiod of 10 hours lit with 400 Watt metal halide power star lamps supplemented with 100 watt tungsten halide lamps. This provided a level of photosynthetically active radiation (PAR) of 113.7 μmoles photons $m^{-2}s^{-1}$ and a red:far red light ration of 2.41. A similar cabinet and lamps were used for the long day. The photoperiod was for 10 hours under the same conditions used for short days and extended for a further 8 hours using only the tungsten halide lamps. In this cabinet the combination of lamps used for the 10 hour period provided a PAR of 92.9 μmoles photons $m^{-2}$ $s^{-1}$ and a red:far red ratio of 1.49. The 8 hour extension produced PAR of 14.27 μmoles $m^{-2}$ $s^{-1}$ and a red:far-red ratio of 0.66.

The flowering times of large populations of plants were measured in the greenhouse. In the summer the plants were simply grown in sunlight. In winter supplementary light was provided so that the minimum daylength was 16 hours.

To measure flowering time, seeds were placed at 4° C. on wet filter paper for 4 days to break dormancy and were then sown on soil. Germinating seedlings were usually covered with cling film or propagator lids for the first 1–2 weeks to prevent dehydration. Flowering time was measured by counting the number of leaves, excluding the cotyledons, in the rosette at the time the flower bud was visible. Leaf numbers are shown with the standard error at 95% confidence limits. The number of days from sowing to the appearance of the flower bud was also recorded, but is not shown. The close correlation between leaf number and flowering time was previously demonstrated for Landsberg erecta and co alleles (Koorneef et al, 1991).

Plant material

The standard wild-type genotype used was *Arabidopsis thaliana* Landsberg erecta. The co-1 mutation was isolated by Redei (1962) and is in an ERECTA background, that in our experiments showed no detectable RFLPs or sequence variation from Landsberg erecta. The co-2 allele was isolated in Landsberg erecta (Koorneef et al, 1991). The details of the lines used for the accurate RFLP mapping of co were described previously (Putterill et al, 1993).

IN all cases described, lines carrying co-2 also carried tt4, although in order not to over-complicate the genotype descriptions in the text this is not mentioned. The tt4 mutation is within the chalcone synthase gene and prevents anthocyanin accumulation in the seed coat, but does not affect flowering time (Koorneef et al, 1983). The mutation is located on chromosome 5, approximately 3.3 cM from co (Putterill et al, 1993). The use of a co-2 tt4 line was useful in confirming that individual plants did carry the co-2 mutation.

RNA extractions

RNA was extracted using a method which is a modified version of that described by Stiekma et al (1988). Approximately 5 g of tissue frozen in liquid nitrogen was ground in a coffee grinder and extracted with a mixture of 15 ml of phenol and 15 ml of extraction buffer (50 mM Tris pH8, 1 mM EDTA, 1% SDS). The mixture was shaken, centrifuged and 25 ml of the aqueous layer recovered. This was then shaken vigorously with a mixture of 0.7 ml 4M sodium chloride, 10 ml phenol and 10 ml of chloroform. The aqueous layer was recovered after centrifugation and extracted with 25 ml of chloroform. The RNA was then precipitated from 25 ml of the aqueous layer by the addition of 2 ml of 10 M LiCL, and the precipitate recovered by centrifugation. The pellet was dissolved in 2 ml DEPC water and the RNA precipitated by the addition of 0.2 ml of 4M sodium chloride and 4 ml of ethanol. After centrifugation the pellet was dissolved in 0.5 ml of DEPC water and the RNA concentration determined.

DNA extractions

Arabidopsis DNA was performed by a CTAB extraction method described by Dean et al (1992).

Isolation of cDNA by RT-PCR

Total RNA was isolated from whole seedlings at the 2–3 leaf stage growing under long days in the greenhouse. For first strand cDNA synthesis, 10 μg of RNA in a volume of 10 μl was heated to 65° C. for 3 minutes, and then quickly cooled on ice. 10 μl of reaction mix was made continuing 1 μl RNAsin, 1 μl of standard $dT_{17}$-adapter primer (1μg/μl; Frohman et al, 1988), 4 μl of 5× reverse transcriptase buffer (250 mM TrisHCl pH8.3, 375 mM KCl, 15 mM $MgCl_2$), 2 μl DTT (100 mM), 1 μl dNTP (20 mM), 1 μl reverse transcriptase (200 units, M-MLV Gibco). This reaction mix was then added to the RNA creating a final volume of 20 μl. The mixture was incubated at 42° C. for 2 hours and then diluted to 200 μl with water.

10 μl of the diluted first strand synthesis reaction was added to 90 μl of PCR mix containing 4 μl 2.5 mM dNTP, 10 μl 10×PCR buffer (Boehringer plus Mg), 1 μl of a 100 ng/μl solution of each of the primers, 73.7 μl of water and 0.3 μl of 5 units/μl Taq polymerase (Boehringer or Cetus Amplitaq). The primers used were CO49 (SEQ ID NO:21) (5'GCTCCCACACCATCAAACTTACTAC 5' end located 38 bp upstream of translational start of CO) and CO50 (SEQ ID NO:22) (5'CTCCTCGGCTTCGATTTCTC 5' end located 57 bp upstream of translational termination codon of CO). The reaction was performed at 94° C. for 1 minute, 34 cycles of 55° C. for 1 minute, 72° C. for 2 minutes and then finally at 72° C. for 10 minutes.

20 μl of the reaction was separated through an agarose gel, and the presence of a fragment of the expected size was demonstrated after staining with ethidium bromide. The DNA was transferred to a filter, and the fragment of interest was shown to hybridise to a short DNA fragment derived from the CO gene. The remainder of the PCR reaction was loaded onto another gel, the amplified fragment was extracted, treated with T4 DNA polymerase and ligated to Bluescript vector (Stratagene) cleaved with EcoRV. The PCR reaction was done in duplicate, and two independently amplified cDNAs were sequenced to ensure that any PCR induced errors were detected.

Isolation of cDNA fragments by 3' RACE

First strand cDNA synthesis was performed using the same conditions, RNA preparation and $dT_{17}$-adapter as described above for RT-PCR. The PRC was then performed using the standard adapter primer (SEQ ID NO:23) (5'gactcgagtcgacatcg; Frohman et al, 1988) and the CO49 primer described above. The PCR conditions were the same as described above, except that the amplification cycle was preceded by a 40 minute extension at 72° C. 20 μl of the reaction was separated through an agarose gel, and a smear of fragments between 550 bp and 1.6 kb in length was detected. The remainder of the reaction was loaded on a similar gel, the region predicted to contain fragments of 1–2 kb was excised, the DNA extracted and subjected to a second round of PCR using the adapter primer and another CO specific primer (CO28 (SEQ ID NO:24), 5'tgcagattctgcctacttgtgc, 5' and located 94 bp downstream of translational start site of CO). When this PCR was monitored on an agarose gel a fragment around the expected size of 1.3 kb was detected. This fragment was extracted from the gel, treated with T4 DNA polymerase and ligated to Bluescript DNA cleaved with EcoRV. Four amplified fragments recovered from two independent amplifications were sequenced entirely. All four were polyadenylated at slightly different positions, as described in the text.

Detection of CO transcript by RT-PCR

First strand synthesis was performed exactly as described above for the method used to isolate a cDNA clone, except that the RNA was isolated from plant grown in controlled environment cabinets at different stages. All samples were harvested and analysed in duplicate.

The primers used to amplify CO cDNA are described in the text and previously in Experimental Procedures. The primers used to amplify the cDNA of the gene used as a control were CO1 (SEQ ID NO:25) (5' TGATTCTGCCTACTTGTGCTC) and CO2 (SEQ ID NO:26) (5' GCTTGGTTTGCCTCTTCATC).

DNA sequencing

The Sanger method was used to sequence fragments of interest inserted in a Bluescript plasmid vector. Reactions were performed using a Sequenase kit (United States Biochemical Corporation).

Isolation of clones containing each of the seven co alleles

DNA was extracted from plants homozygous for each of the alleles. Approximately 1 ng of genomic DNA was diluted to 10 µl with water and added to 90 µl of reaction mix, as described above except that primers CO41 (SEQ ID NO:27) (5'ggtcccaacgaagaagtgc 5' end located 263 bp upstream of translational start codon of CO) and CO42 (SEQ ID NO:28) (5'cagggaggcgtgaaagtgt 5' end located 334 bp downstream of translational stop codon of CO) were used. The PCR conditions were: 94° C. for 3 minutes, followed by 34 cycles of 94° C. for 1 minute, 55° C. for 1 minute, 72° C. for 2 minutes and then finally 72° C. for 10 minutes. In each case this produced a major fragment of the expected size, 1.95 kb. The PCR was carried out in duplicate for each allele. In each case the reactions were extracted with phenol and chloroform, ethanol precipitated and treated with T4 DNA polymerase. The reactions were then separated through an agarose gel, the fragment purified and ligated to SK+Bluescript cleaved with EcoRV. Ligations were introduced into *E. coli* DH5 alpha and the recombinant plasmids screened by colony PCR for those carrying an insertion of the expected size. The DNA sequences of two independently amplified fragments derived from each allele was determined.

Screening phase and cosmid libraries

A lysate of the cosmid library (Olszewski and Ausubel, 1988) was used to infect *E. coli* DH5 alpha, and twenty thousand colonies were screened with the probes described in the text. Three cDNA libraries were screened to try to identify a CO cDNA. The number of plaques screened were $5 \times 10^5$ from the "aerial parts" library (supplied by EC Arabidopsis Stock Center, MPI, Cologne), $3 \times 10^5$ plaques of a library made from plants growing in sterile beakers (made by Dr A. Bachmair and supplied by the EC Arabidopsis Stock Center) and $1 \times 10^6$ plaques of the CD4-71-PRL2 library (supplied by the Arabidopsis Biological Resource Center at Ohio State University).

Transformation of Arabidopsis

The cosmids containing DNA from the vicinity of CO were mobilised into *Agrobacterium tumefaciens* C58C1, and the T-DNA introduced into Arabidopsis plants as described by Valvekens et al, 1988. Roots of plants grown in vitro were isolated and grown on callus-inducing medium (Valvekens et al, 1988) for 2 days. The roots were then cut into short segments and co-cultivated with *Agrobacterium tumefaciens* carrying the plasmid of interest. The root explants were dried on blotting paper and placed onto callus-inducing medium for 2–3 days. The Agrobacterium were washed off, the roots dried and placed onto shoot inducing medium (Valvekens et al, 1988) containing vancomycin to kill the Agrobacterium and kanamycin to select for transformed plant cells. After approximately 6 weeks green calli on the roots start to produce shoots. These are removed and placed in petri dishes or magenta pots continuing germination medium (Valvekens et al, 1988). These plants produce seeds in the magenta pots. These are then sown on germination medium containing kanamycin to identify transformed seedlings containing the transgene (Valvekens et al, 1988).

EXAMPLE 2

Construction of promoter fusions to the CO open reading frame

A PvuII-EcoRV fragment containing the entire CO gene was inserted into the unique EcoRV site of the Bluescript™ plasmid. The CO gene fragment was inserted in the orientation such that the end defined by the EcoRV site was adjacent to the HindIII site within the Bluescript™ polylinker. This plasmid was called pCO1. The PvuII-EcoRV fragment inserted in pCO1 contains two HindIII sites both 5' of the point at which translation of the CO protein is initiated. Cleavage of pCO1 with HindIII produces a fragment that contains the entire CO open reading frame from 63 bp upstream of the initiation of translation to the PvuII site which is downstream of the polyadenylation site, as well as all of the bluescript vector from the PvuII/EcoRV junction created by the ligation event to the HindIII site within the polylinker. Ligation of a promoter containing fragment in the appropriate orientation to this fragment creates a fusion of the promoter to the CO open reading frame. For instance, a variety of promoters may be inserted at this position, as discussed below.

A GSTII promoter fusion to the CO open reading frame

The GSTII promoter-containing fragment was derived from plasmid pGIE7 (supplied by Zeneca) as a HindIII-NdeI fragment, whose sequence is shown in FIG. 2 (SEQ ID NO:3). An oligonucleotide adapter (SEQ ID NO:29) (5' TACAAGCTTG) was inserted at the NdeI site to convert it into a HindIII site. The resutling plasmid was then cleaved with HindIII, and the promoter containing fragment ligated to the HindIII fragment containing the CO open reading frame. A recombinant plasmid that contained the GSTII promoter in the orientation such that transcription would occur towards the CO open reading frame was identified by PstI digestion. The GSTII-CO fusion was then moved into a binary vector described by Jones et al (1992) as a ClaI-XbaI fragment.

The binary vector may be introduced into an *Agrobacterium tumefaciens* strain and used to introduce the fusion into dicotyledonous species, or the fusion may be introduced into monocotyledonous species by a naked DNA transformation procedure. Protocols for transformation have been established for many species, as discussed earlier.

The GSTII promoter may be used to induce expression of the CO gene by application of an exogenous inducer such as the herbicide safeners dichloramid and flurazole, as described in WO93/01294 (Imperial Chemical Industries Limited).

A heat shock promoter fusion to the CO open reading frame

An alternative inducible system makes use of the well characterised soybean heat shock promoter. Gmhsp17.3B, which is induced by expression in response to exposure to high temperatures in a variety of plant species (discussed by Balcells et al, 1994). The promoter is available as a 440 bp XbaI-XhoI fragment (Balcells et al, 1994) which after treatment with T4 DNA polymerase may be inserted into pCO1 cleaved with HindIII, as described above for the GSTII fusion. The resutling fusion may then be introduced into the binary vector, *Agrobacterium tumefaciens* and transgenic plants, as described earlier. CO expression may be induced by exposing plants to temperatures of approximately 40° C.

Fusion to the CO gene of a modified CaMV 35S promoter containing tetracycline resistance gene operators A modified CaMV 35S promoter which contains three operators from the bacterial tetracycline resistance gene has been developed as a chemically indelible system. In the presence of the tetracycline gene repressor protein this promoter is inactive, but this repression is overcome by supplying plants with tetracycline (Gatz et al, 1992). This is an alternative chemically indelible promoter which may be fused to the CO open reading frame. The promoter is available as a SmaI-XbaI fragment (Gatz et al, 1992) which after treatment with T4 DNA polymerase may be inserted into pCO1 cleaved with HindIII as described earlier. After introduction of this fusion into plants also containing the repressor gene, CO expression may be induced by supplying the plants with tetracycline.

A CaMV 35S promoter fusion to the CO open reading frame

The CaMV 35S promoter was isolated from plasmid pJIT62 (physical map of which is shown in FIG. 4). The KpnI-HindIII fragment containing the CamV 35S promoter was fused to the CO open reading frame by ligation to plasmid pCOI cleaved with HindIII and KpnI. The single KpnI site was then converted to a ClaI site by insertion of an adapter oligonucleotide (SEQ ID NO:30) (5'TATCGATAGTAC), and then a ClaI-BamHI fragment containing the promoter fused to the CO ORF was inserted into a binary vector. The fusion may be introduced into transgenic plants either by the use of *Agrobacterium tumefaciens* or as naked DNA, as described earlier.

Fusion of the meri 5 promoter to the CO open reading frame

The meri 5 promoter is available as a 2.4 kb BglII-StuI fragment (Medford et al, 1991). This may be treated with T4 DNA polymerase and inserted into the HindIII site of pCO1 as described above. The fusion may then be introduced into transgenic plants, as described above.

EXAMPLE 3

Flowering time under short days of plants carrying extra copies of CO

Under short day conditions wild type plants and co-2 homozygotes both flower at approximately the same time (Table 1), suggesting that the CO product is not required for flowing under these conditions. However, under short days, several of the co-2 tt4 families carrying the T-DNAs derived from cosmids B and C flowered earlier than both the parental co-2 line and wild type (Table 1). In particular, 2 lines (4 and 6) carrying cosmid C flowered much earlier than wild type. This suggested that in some families a transgenic copy of CO was expressed at a higher level than the original copy, or expressed ectopically, and that this led to earlier flowering under short days than that of wild type plants.

Cosmid B was also introduced into wild-type Landsberg erecta plants and T2 plants homozygous for the transgene at a single locus were identified in the same way as described above (Table 1). Of the 3 independent transformants anlaysed in the T3 generation, one flowered slightly earlier than wild-type plants under long days, and significantly earlier under short days (Table 1). This again suggested that at least at some chromosomal locations, extra copies of the CO gene can cause early flowering.

EXAMPLE 4

Influencing flowering characteristics using a CaMV 35S promoter/CO gene fusion

A fusion of a CaMV 35S promoter to the CO open reading frame was introduced into co mutant Arabidopsis plants.

First the ClaI-BamH1 fragment described in Example 2 was inserted into the ClaI-BamH1 sites of binary vector SLJ1711 (Jones et al., 1992). An *Agrobacterium tumefaciens* strain carrying this vector was then used for transformation of Arabidopsis root explants, followed by regeneration of transformed plants as described by Valvekens et al. (1988).

The resulting transgenic plants flowered significantly earlier than wild-type under both inductive and non-inductive conditions. For example, under inductive long-day conditions, wild-type plants flowered after forming approximately 5 leaves, while the transgenic plants flowered with 3–4 leaves. Under non-inductive short days, wild-type plants flowered with approximately 20 leaves, while the transgenic plants formed 3–4 leaves. The use of promoter fusions to increase the abundance of the CO mRNA, or to alter the specificity of CO transcription, can therefore be used to lead to dramatically earlier flowering than that of wild-type plants.

In addition, some of the transgenic plants carrying the fusion of the CaMV 35S promoter to the CO gene formed a terminal flower at the end of the shoot. The shoot of wild-type plants shows indeterminate growth, growing and forming flowers on the sides of the shoot indefinitely. However, terminal flower (tfl) mutants show determinate growth, terminating shoot development prematurely by forming a flower at the apex of the shoot. In wild-type plants, the TFL gene is thought to prevent the formation of flowers at the apex of the shoot, by preventing the expression of genes that promote flower development, such as LEAFY (LFY), in the apical cells. This is supported by the observations that LFY is expressed in the shoot apex of tfl mutants but not wild type plants, and that fusions of the CaMV 35S promoter to LFY cause transgenic plants to form a terminal flower (Weigel and Nilsen, 1995). While not intending to be bound by any particular theory, the fusion of CO to the CaMV 35S promoter might therefore cause a terminal flower by activating genes such as LFY at the apex of the shoot.

The two phenotypes caused by the CO fusion to the CaMV 35S promoter, early flowering and the formation of a terminal flower, may be separated by the use of other promoters. For example, terminal flower formation might be optimised by using a promoter, such as that of the meri 5 gene mentioned above, that is expressed mainly in the apical meristem, while early flowering without a terminal flower might result from expressing the gene from the promoters that are not well expressed in the apical meristem, such as a heat-shock promoter.

EXAMPLE 5

Cloning of a CO homologue from *Brassica napus*

Low stringency hybridizations (Sambrook et al., 1989) were used to screen a lambda genomic DNA library made from *Brassica napus* DNA. Positively hybridizing clones were analysed and classified by constructing maps of their restriction enzyme cleavage sites (using HindIII, XhoI, EcoRV, XbaI, EcoRI and NdeI) CO homologues were distinguished from other members of the CO gene family because of the similarity of their restriction enzyme map with that of the Arabidopsis CO gene, and because a second gene that is located close to CO in the Arabidopsis genome was shown to be present at a similar position in the Brassica clones. Two CO homologues, corresponding to the genes present on *Brassica napus* linkage groups N10 and N19 (Sharpe et al., 1995), were then sub-cloned into plasmids and sequenced. The sequence of the gene from the N10 linkage group is shown in FIG. 5 (SEQ ID NO:5) and that from the N19 linkage group is shown in FIG. 6 (SEQ ID NO:7). The amino acid sequences of the proteins encoded by these genes are very similar to that of the Arabidopsis CO gene, particularly in the regions demonstrated by mutagenesis to be important for the functioning of the protein; 86 amino acids across the zinc-finger region are 84% identical, and a 50 amino acid region at the carboxy terminus of the protein, that is affected in two of the Arabidopsis mutants, is 88% identical. These two regions are the most conserved, with the intervening 187 amino acids from the middle of the protein being 64% identical.

This sequence analysis indicates that CO homologues can be isolated from plant species other than Arabidopsis. In addition, restriction fragment length polymorphism mapping strongly suggests that CO homologues are important in regulating flowering time of other species. For example, in *Brassica nigra* a CO homologue closely co-segregates with a major quantitative trait locus for flowering time (U. Lagercrantz et al, in press), and in *Brassica napus* CO homologues mapping to linkage groups N2 and N12 co-segregate with allelic variation for flowering time.

TABLE 1

Flowering time and segregation of kanamycin resistance in T2 and T3 generations of co-2 carrying the T-DNA of cosmid B or C plants

| Transgenic co tt4 line scored | Ratio of Km resistant seedlings in T2[1] | Average LN at flowering of T3 individual under LDs[2] | Average LN at flowering of T3 individual under SDs[2] | Ratio of Km resistant seedlings in T3 |
|---|---|---|---|---|
| cosmid B line 1 | 3:1 | 4.6+/−0.4 | 14.0+/−2.5 | 1:0 |
| cosmid B line 2 | 3.7:1 | 4.2+/−0.3 | 18.5+/−1.1 | 1:0 |
| cosmid B line 3 | 2.9:1 | 4.6+/−0.8 | 13.5+/−4.1 | 1:0 |
| cosmid B line 4 | 2.4:1 | 4.6+/−0.8 | 16.4+/−2.2 | 1:0 |
| cosmid B line 5 | 3.0:1 | 5.1+/−0.5 | 18.5+/−1.1 | 1:0 |
| cosmid C line 1 | 2.9:1 | 4.6+/−0.6 | 20.6+/−3.8 | 1:0 |
| cosmid C line 2 | 3.4:1 | 3.9+/−0.4 | 11.7+/−3.2 | 1:0 |
| cosmid C line 3 | 3.3:1 | 4.0+/−0.4 | 20.4+/−1.2 | 1:0 |
| cosmid C line 4 | 4.9:1 | 3.7+/−0.3 | [3]7.6+/−5.3 | 1:0 |
| cosmid C line 5 | 3:1 | 4.9+/−0.6 | 17.7+/−2.1 | 1:0 |
| cosmid C line 6 | 3.8:1 | 3.5+/−0.5 | 6.6+/−1.4 | 1:0 |
| Landsberg erecta | — | 5.1+/−0.8 | 18.9+/−2.4 | — |
| co-2 | — | 12.4+/−1.0 | 18.1+/−3.4 | — |

[1] Over 80 plants were tested in each family, except for cosmid B line 3 in which 35 plants were used.
[2] 10 plants from each family were tested
[3] The large standard error in this population was due to 2 plants that flowered with 18 leaves, while the other 8 has a leaf number of 5.1+/−1 at flowering. Southern analysis of this line using a T-DNA fragment as probe identified 6 hybridising fragments. The variation in flowing time could therefore be due to the segregation of one T-DNA copy that is required for early flowering, or to the occurrence of co-suppression repressing activity of the transgenes in some individuals.

Flowering time was measured by counting the number of leaves present at the time that the flower bud appeared in the centre of the rosette (Koorneef et al, 1991) Experimental Procedures).

TABLE 2

Flowering time of transgenic wild-type plants carrying extra copies of the CO gene

| Landsberg erecta transgenic line | Km in T2[1] | Average LN at flowering of T3 individuals under LDs[2] | Average LN at flowering of T3 individuals under SDs[2] | Ratio of kanamycin resistance in T3 |
|---|---|---|---|---|
| cosmid B line 1 | 3.4:1 | 4.4+/−1.0 | 18.1+/−2.1 | 1:0 |
| cosmid B line 2 | 5.9:1 | 3.2+/−0.6 | 10.1+/−2.2 | 1:0 |
| cosmid B line 3 | 2.8:1 | 4.0+/−0.5 | 19.6+/−2.2 | 1:0 |
| Landsberg erecta | | 5.1+/−0.8 | 18.9+/−2.4 | — |
| co-2 | | 12.4+/−1.0 | 18.1+/−3.7 | — |

[1] Over 80 plants were tested in each family.
[2] 10 plants from each family were tested.

REFERENCES

Balcells et al., (1994) The Plant Journal 5, 755–764.
Bancroft I, Wolk CP (1988) Nucl. Acids Res. 16:7405–7418
Benfey et al., EMBO J 9:1677–1684 (1990a).
Benfey et al., EMBO J 9:1685–1696 (1990b).
Becker et al., (1994) The Plant Journal 5, 299–307.
Bower, R. and Birch, R. G. (1992) The Plant Journal 2, 409–416.
Brendel, V. and Karlin, S. (1989) Proc Natl Acad Sci USA 86, 5698–5702.
Cao et al., (1992) Plant Cell Reports 11, 586–591.
Chang et al., (1988) Proc Natl Acad Sci USA 85:6856–6860
Christou et al., (1991) Bio/Technol. 9, 957–962.
Coulson et al., (1988) Nature 335:184–186
Dale, P. J. and Irwin, J. A. (1994) in Designer oil crops ed. Murphy D. J. VCH, Weinheim, Germany.
Datta et al., (1990) Bio/Technol. 8, 736–740.
Dean et al., (1992) in *Arabidopsis thaliana*. Plant Journal 2, 69–82.
Frohman et al., (1988) Proc Natl Acad Sci USA 85, 8998–9002.
Gatz et al., (1992) Plant Journal 2, 397–404.
Gill, G. and Ptashne, M. (1988) Nature 334, 721–724.
Gordon-Kamm et al., Plant Cell 2, 603–618.
Heard et al., (1989) Nucl Acids Res 17:5861
Jones et al., (1992) Transgenic Research 1, 285–297.
Koornneef et al., (1991) Mol Gen Genet 229, 57–66.
Koornneef et al., (1983) Heredity 74, 265–272.
Koziel et al., (1993) Bio/Technol. 1, 194–200.
Lagercrantz, U., Putterill, J., Coupland, G. and Lydiate D. (1995) comparative mapping in Arabidopsis and Brassica, fine scale genome collinearity and congruence of genes controlling flowering time. Plant Journal in press.
Lee et al., (1994) The Plant Cell 6, 75–83.
Martin, D. I, K. and Orkin, S. H. (1990) Genes and Development 4, 1886–1898.
Medford, J. I. (1992) Plant Cell 4, 1029–1039.
Medford et al., (1991) Plant Cell 3, 359–370.
Moloney et al., (1989) Plant Cell Reports 8, 238–242.
Napoli et al., (1990) The Plant Cell 2, 279–289.
Olszewski, N. and Ausubel, F. M. (1988) Nucleic Acids Res. 16, 10765–10782.
Potrykus (1990) Bio/Technology 8, 535–542.
Ptashne, M. and Gann, A. F. (1990) Nature 346, 329–331.

Putterill et al., (1993) Mol Gen Genet 239, 145–157.
Putterill et al., (1995) Cell 80, 847–857.
Radke et al., (1988) Theoretical and Applied Genetics 75, 685–694.
Ramain et al., (1993) Development 119, 1277–1291.
Redei, G. P. (1962) Genetics 47, 443–460.
Relichová J (1976) Arabidopsis Inf Serv 13:25–28
Rhodes et al., (1988) Science 240, 204–207.
Rothstein et al., (1987) Proc. Natl. Acad. Sci. USA 84, 8439–8443.
Sambrook et al., (1989). Molecular Cloning: A Laboratory Manual. (Cold Spring Harbor, N.Y.: Cold Spring Harbor Laboratory).
Sánchez-García, I. and Rabbits, T. H. (1994) Trends in Genetics 10, 315–320.
Schmidt R, Dean C (1992) Genome Analysis Vol. 4 Strategies for physical mapping Cold Spring Harbour Laboratory Press 71–98.
Schmidt R et al., (1992) Aust J Plant Physiol 19: 341–351
Sharpe et al., (1995) Frequent non-reciprocal translocation in the amphidiploid genome of oilseed rape (*Brassica napus*). Genomics in press.
Shimamoto et al., (1989) Nature 338, 2734–2736.
Smith et al., (1988) Nature 334, 724–726.
Somers et al., (1992) Bio/Technol. 10, 1589–1594.
Stiekema et al., (1988) Plant Molecular Biology 11, 255–269.
Tai T, Tanksley S (1991) Plant Mol Biol Rep.8:297–303
Trainor et al., (1990) Nature 343, 92–96.
van der Krol et al., (1990) The Plant Cell 2, 291–299.
Vais et al., (1992) Bio/Technol. 10, 667–674.
Valvekens et al., (1988) Proc. Natl. Acad. Sci. USA 87, 5536–5540.
Weigel et al., (1992) Cell 69, 843–859.
Weigel and Nilssen (1995) A development switch sufficient for flower initiation in diverse plants. Nature in press.
Zhang et al., (1992) The Plant Cell 4, 1575–1588.

We claim:

1. An isolated nucleic acid having a nucleotide sequence coding for a polypeptide which comprises the amino acid sequence shown in SEQ ID NO:2.

2. Nucleic acid according to claim 1 wherein the coding sequence is the coding sequence shown in SEQ ID NO:1.

3. An isolated nucleic acid encoding a CO homologue, CO having the amino acid sequence shown in SEQ ID NO:2, wherein the homologue is a Brassica homologue, comprises an arrangement of cysteines characteristic of zinc fingers, the nucleic acid positively hybridizes in Southern hybridization experiments to an *Arabidopsis thaliana* CO probe, of which probe the coding strand nucleotide sequence is shown in SEQ ID NO:1, and wherein expression of said homologue advances flowering time in a transgenic plant, timing of flowering in the plant being substantially unaffected by vernalization.

4. Nucleic acid according to claim 3 able to complement a co mutation.

5. Nucleic acid according to claim 4 wherein said mutation is in *Arabidopsis thaliana*.

6. Nucleic acid according to claim 3 wherein the arrangement of cysteines is $C-X_2-C-X_{16}-C-X_2-C$.

7. Nucleic acid according to claim 3 wherein the encoded polypeptide comprises a zinc finger.

8. Nucleic acid according to claim 3 wherein said homologue has the amino acid sequence shown in SEQ ID NO:6 or SEQ ID NO:8.

9. Nucleic acid according to claim 8 wherein said coding sequence is the coding sequence shown in SEQ ID NO:5 or SEQ ID NO:7.

10. Nucleic acid according to claim 3 under the control of a regulatory sequence for expression of said polypeptide.

11. Nucleic acid according to claim 10 wherein said regulatory sequence comprises an inducible promoter.

12. Nucleic acid according to claim 11 wherein the promoter is derived from a maize gene for a 27 kD sub-unit of gluthathione-S-transferase, isoform II.

13. A nucleic acid vector suitable for transformation of a plant cell and comprising nucleic acid according to claim 1.

14. A plant cell comprising heterologous nucleic acid according to claim 3.

15. Nucleic acid according to claim 14 wherein said heterologous nucleic acid is within the genome of the plant cell.

16. A plant cell according to claim 15 having more than one said nucleotide sequence per haploid genome.

17. A plant comprising plant cell according to claim 14.

18. A method of advancing flowering time of a plant, the method comprising causing or allowing expression of the polypeptide encoded by nucleic acid according to claim 3 from that nucleic acid within cells of the plant, which nucleic acid is heterologous to the cells.

19. Nucleic acid according to claim 1 under the control of a regulatory sequence for expression of said polypeptide.

20. A plant cell comprising heterologous nucleic acid according to claim 1.

21. A plant cell according to claim 20 wherein said heterologous nucleic acid is within the genome of the plant cell.

22. A plant comprising plant cells according to claim 20.

23. A method of advancing flowing time of a plant, the method comprising causing or allowing expression of the polypeptide encoded by nucleic acid according to claim 1 from that nucleic acid within cells of the plant, which nucleic acid is heterologous to the cells.

24. A nucleic acid vector suitable for transformation of a plant cell and comprising nucleic acid according to claim 3.

* * * * *

SEQUENCE LISTING

```
(1) GENERAL INFORMATION:

(iii) NUMBER OF SEQUENCES: 31

(2) INFORMATION FOR SEQ ID NO: 1:

(i) SEQUENCE CHARACTERISTICS:
        (A) LENGTH: 1124 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Arabidopsis thaliana
        (B) STRAIN: Landsberg erecta (viii) POSITION IN GENOME:
        (A) CHROMOSOME/SEGMENT: chromosome 5

(ix) FEATURE:
        (A) NAME/KEY: CDS
        (B) LOCATION:1..1119

(xi) SEQUENCE DESCRIPTION: SEQ ID NO: 1:

ATG TTG AAA CAA GAG AGT AAC GAC ATA GGT AGT GGA GAG AAC AAC AGG        48
Met Leu Lys Gln Glu Ser Asn Asp Ile Gly Ser Gly Glu Asn Asn Arg
 1               5                  10                  15

GCA CGA CCC TGT GAC ACA TGC CGG TCA AAC GCC TGC ACC GTG TAT TGC        96
Ala Arg Pro Cys Asp Thr Cys Arg Ser Asn Ala Cys Thr Val Tyr Cys
             20                  25                  30

CAT GCA GAT TCT GCC TAC TTG TGC ATG AGC TGT GAT GCT CAA GTT CAC       144
His Ala Asp Ser Ala Tyr Leu Cys Met Ser Cys Asp Ala Gln Val His
         35                  40                  45

TCT GCC AAT CGC GTT GCT TCC CGC CAT AAA CGT GTC CGG GTC TGC GAG       192
Ser Ala Asn Arg Val Ala Ser Arg His Lys Arg Val Arg Val Cys Glu
     50                  55                  60

TCA TGT GAG CGT GCT CCG GCT GCT TTT TTG TGT GAG GCA GAT GAT GCC       240
Ser Cys Glu Arg Ala Pro Ala Ala Phe Leu Cys Glu Ala Asp Asp Ala
 65                  70                  75                  80
```

```
TCT CTA TGC ACA GCC TGT GAT TCA GAG GTT CAT TCT GCA AAC CCA CTT        288
Ser Leu Cys Thr Ala Cys Asp Ser Glu Val His Ser Ala Asn Pro Leu
            85                  90                  95

GCT AGA CGC CAT CAG CGA GTT CCA ATT CTA CCA ATT TCT GGA AAC TCT        336
Ala Arg Arg His Gln Arg Val Pro Ile Leu Pro Ile Ser Gly Asn Ser
                100                 105                 110

TTC AGC TCC ATG ACC ACT ACT CAC CAC CAA AGC GAG AAA ACA ATG ACC        384
Phe Ser Ser Met Thr Thr Thr His His Gln Ser Glu Lys Thr Met Thr
            115                 120                 125

GAT CCA GAG AAG AGA CTG GTG GTG GAT CAA GAG GAA GGT GAA GAA GGT        432
Asp Pro Glu Lys Arg Leu Val Val Asp Gln Glu Glu Gly Glu Glu Gly
        130                 135                 140

GAT AAG GAT GCC AAG GAG GTT GCT TCG TGG CTG TTC CCT AAT TCA GAC        480
Asp Lys Asp Ala Lys Glu Val Ala Ser Trp Leu Phe Pro Asn Ser Asp
145                 150                 155                 160

AAA AAT AAC AAT AAC CAA AAC AAT GGG TTA TTG TTT AGT GAT GAG TAT        528
Lys Asn Asn Asn Asn Gln Asn Asn Gly Leu Leu Phe Ser Asp Glu Tyr
                165                 170                 175

CTA AAC CTT GTG GAT TAC AAC TCG AGT ATG GAC TAC AAA TTC ACA GGT        576
Leu Asn Leu Val Asp Tyr Asn Ser Ser Met Asp Tyr Lys Phe Thr Gly
            180                 185                 190

GAA TAC AGT CAA CAC CAA CAA AAC TGC AGC GTA CCA CAG ACG AGC TAC        624
Glu Tyr Ser Gln His Gln Gln Asn Cys Ser Val Pro Gln Thr Ser Tyr
        195                 200                 205

GGG GGA GAT AGA GTT GTT CCG CTT AAA CTT GAA GAA TCA AGG GGC CAC        672
Gly Gly Asp Arg Val Val Pro Leu Lys Leu Glu Glu Ser Arg Gly His
    210                 215                 220

CAG TGC CAT AAC CAA CAG AAT TTT CAG TTC AAT ATC AAA TAT GGC TCC        720
Gln Cys His Asn Gln Gln Asn Phe Gln Phe Asn Ile Lys Tyr Gly Ser
225                 230                 235                 240

TCA GGG ACT CAC TAC AAC GAC AAT GGT TCC ATT AAC CAT AAC GCA TAC        768
Ser Gly Thr His Tyr Asn Asp Asn Gly Ser Ile Asn His Asn Ala Tyr
                245                 250                 255

ATT TCA TCC ATG GAA ACT GGT GTT GTG CCG GAG TCA ACA GCA TGT GTC        816
Ile Ser Ser Met Glu Thr Gly Val Val Pro Glu Ser Thr Ala Cys Val
            260                 265                 270

ACA ACA GCT TCA CAC CCA AGA ACG CCC AAA GGG ACA GTA GAG CAA CAA        864
Thr Thr Ala Ser His Pro Arg Thr Pro Lys Gly Thr Val Glu Gln Gln
        275                 280                 285

CCT GAC CCT GCA AGC CAG ATG ATA ACA GTA ACA CAA CTC AGT CCA ATG        912
Pro Asp Pro Ala Ser Gln Met Ile Thr Val Thr Gln Leu Ser Pro Met
    290                 295                 300

GAC AGA GAA GCC AGG GTC CTG AGA TAC AGA GAG AAG AGG AAG ACA AGG        960
Asp Arg Glu Ala Arg Val Leu Arg Tyr Arg Glu Lys Arg Lys Thr Arg
305                 310                 315                 320

AAA TTT GAG AAG ACA ATA AGG TAT GCT TCG AGG AAG GCA TAT GCA GAG       1008
Lys Phe Glu Lys Thr Ile Arg Tyr Ala Ser Arg Lys Ala Tyr Ala Glu
                325                 330                 335

ATA AGA CCG CGG GTC AAT GGC CGG TTC GCA AAG AGA GAA ATC GAA GCC       1056
Ile Arg Pro Arg Val Asn Gly Arg Phe Ala Lys Arg Glu Ile Glu Ala
            340                 345                 350

GAG GAG CAA GGG TTC AAC ACG ATG CTA ATG TAC AAC ACA GGA TAT GGG       1104
Glu Glu Gln Gly Phe Asn Thr Met Leu Met Tyr Asn Thr Gly Tyr Gly
        355                 360                 365

ATT GTT CCT TCA TTC TGATA                                             1124
Ile Val Pro Ser Phe
370
```

(2) INFORMATION FOR SEQ ID NO: 2:

(i) SEQUENCE CHARACTERISTICS:
    (A) LENGTH: 373 amino acids
    (B) TYPE: amino acid
    (D) TOPOLOGY: linear (ii) MOLECULE TYPE: protein (xi) SEQUENCE DESCRIPTION: SEQ ID NO: 2:

```
Met Leu Lys Gln Glu Ser Asn Asp Ile Gly Ser Gly Glu Asn Asn Arg
 1               5                  10                  15

Ala Arg Pro Cys Asp Thr Cys Arg Ser Asn Ala Cys Thr Val Tyr Cys
             20                  25                  30

His Ala Asp Ser Ala Tyr Leu Cys Met Ser Cys Asp Ala Gln Val His
         35                  40                  45

Ser Ala Asn Arg Val Ala Ser Arg His Lys Arg Val Arg Val Cys Glu
     50                  55                  60

Ser Cys Glu Arg Ala Pro Ala Ala Phe Leu Cys Glu Ala Asp Asp Ala
 65                  70                  75                  80

Ser Leu Cys Thr Ala Cys Asp Ser Glu Val His Ser Ala Asn Pro Leu
             85                  90                  95

Ala Arg Arg His Gln Arg Val Pro Ile Leu Pro Ile Ser Gly Asn Ser
            100                 105                 110

Phe Ser Ser Met Thr Thr Thr His His Gln Ser Glu Lys Thr Met Thr
        115                 120                 125

Asp Pro Glu Lys Arg Leu Val Val Asp Gln Glu Gly Glu Glu Gly
    130                 135                 140

Asp Lys Asp Ala Lys Glu Val Ala Ser Trp Leu Phe Pro Asn Ser Asp
145                 150                 155                 160

Lys Asn Asn Asn Gln Asn Asn Gly Leu Leu Phe Ser Asp Glu Tyr
                165                 170                 175

Leu Asn Leu Val Asp Tyr Asn Ser Ser Met Asp Tyr Lys Phe Thr Gly
            180                 185                 190

Glu Tyr Ser Gln His Gln Gln Asn Cys Ser Val Pro Gln Thr Ser Tyr
        195                 200                 205

Gly Gly Asp Arg Val Val Pro Leu Lys Leu Glu Glu Ser Arg Gly His
    210                 215                 220

Gln Cys His Asn Gln Gln Asn Phe Gln Phe Asn Ile Lys Tyr Gly Ser
225                 230                 235                 240

Ser Gly Thr His Tyr Asn Asp Asn Gly Ser Ile Asn His Asn Ala Tyr
                245                 250                 255

Ile Ser Ser Met Glu Thr Gly Val Val Pro Glu Ser Thr Ala Cys Val
            260                 265                 270

Thr Thr Ala Ser His Pro Arg Thr Pro Lys Gly Thr Val Glu Gln Gln
        275                 280                 285

Pro Asp Pro Ala Ser Gln Met Ile Thr Val Thr Gln Leu Ser Pro Met
    290                 295                 300

Asp Arg Glu Ala Arg Val Leu Tyr Arg Glu Lys Arg Lys Thr Arg
305                 310                 315                 320

Lys Phe Glu Lys Thr Ile Arg Tyr Ala Ser Arg Lys Ala Tyr Ala Glu
                325                 330                 335

Ile Arg Pro Arg Val Asn Gly Arg Phe Ala Lys Arg Glu Ile Glu Ala
            340                 345                 350

Glu Glu Gln Gly Phe Asn Thr Met Leu Met Tyr Asn Thr Gly Tyr Gly
        355                 360                 365
```

```
Ile Val Pro Ser Phe
    370

(2) INFORMATION FOR SEQ ID NO: 3:

(i) SEQUENCE CHARACTERISTICS:
        (A) LENGTH: 2493 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Zea mays (xi) SEQUENCE DESCRIPTION: SEQ ID NO: 3:

AAGCTTGGGC GTAGGTGTTG TCTATCGGCG AAAACACGCG CGGTACGCCA AGAACAGCGC      60

GGCCATCTCC ATCCCAGGCA CGGTGCGCCC GCTTTTTCGC CGTCTCGCTG AGTCACGGCG     120

GGCGTCCAGC AGGTAGTTGA GCGCCTTCCG CGGCACGAAT CGCTGCGTGC GGCCCGGATC     180

TGGTCGAGTT GGTAGTCAGC GTCGGTGTCG AATGCCGGGA CGTCGACCAG GAAGAAGTTG     240

CCGTCGCTGG GGTGGGGACG GAAGGCGTCA GGATTGTCGC AAGGGCAGAG CCCAGCCTGC     300

GGGCGGGGCT ACCTCGTCGA CGCCTCGGCA CGGCGGCGG AAAGCTGCTG CGGGACGTGC      360

CCGCCTGGGC CGCCTTCTCG GTGAAGTGGT CCTCGAAGGG GACGAGCTCG CTGGGGTCAA     420

ACCACCCCAT AGCTCGAGTC ACCGAAGAAG GCGACGAGGA CGAGCCCGTC GCGGTGGCCG     480

CGGTGTACCT CCTCGTCGTC GGTGAGGCTG ACGCTGTAGA TATGGCCAGG CCACCACGGA     540

TGGGACTTCA CCTTGGCCCA GACCATGTCG CCGAACCGGG GGCCGCCGTT CGCCCATGCG     600

ATGCCGCGTC CGGCAGCAGG AACCATGGCG CCTCCAGCGG CGGGGTCGGA CATCCTGTGG     660

AGGGGAACCG AAAACCTAGA TTTGGATGCA GGTTCGATTG GTCTGGGCTT GGGTTTGGGT     720

TCCGGAGGAG GGTGGCCTGG GATCGGTGGA AGGAGGGACA TTGTTGGTAA TTTTTATTAT     780

TTTATAATAT GGAGAAATTC GAGAGACTGA ACGATGGTGA TGTTTATTTG AGGACTATGT     840

AGTATAAAGT GTAAAATAGT ATTTTATCAA GTTTATATTC ACGTTTTTGC TGAAGATAGT     900

ATAATAGTGG AGTTGTTTTT GGCGGCTACA TAATCTTAGG CTATCTTCTC GGTCGCTCTC     960

ATATCATATC TACTATCACA TTCTCTATTT TAAATTTCAC TTTGTGTAAT CTACACTATA    1020

AAATAGTGTT TTACACGGTA TGTTGTACAC AGCCTTATCG TGGCGCGACG GAGTTGGATA    1080

GAGATGGTGA ACAGCTGGAT AGATATGATT TATAGGCGAT TGGGTAGATG TGATTTGATA    1140

GGTGGTTATG TAGGAGCGAT TTAGTGAGAC ATTGTAAATA ATTAGGTTGA TGTGATCCGA    1200

GGATGGCTAG GTAGATATGA TTTTAATGGA TGGTTTGGTG GACTAAGTTA TGTGGACATT    1260

ATAATATGTT TTAAATTTCT AAGAAATTGT TTGTGTTAAA TTGTATCCCA CATAGATTAT    1320

TTAGCCATCT CAAAGAGAGG TTTGGGTTGT TTACACAAAT AAAATATTCG TTTGCTTCTA    1380

CAATTTATAT GTTTTTTATT TACATGAAAA CTATATTTTT TATTCATCTA CTCACCCAGC    1440

ACAGAAATTC TGGTTGAGTA GATGAAAAAA AACTACAACA AACTCTTCCT GAAAGTGTCG    1500

GTGTGAAGCC GAGAAATCCT TTTCATTTCG GTGACGGAGC CCCTTGCTGG CTGCTGCTCA    1560

GTGCACTCCG TTCGCCTGCC TGCCACTACA AGCGACGGCC GACGACTCGC AAGTATCGGT    1620

AGGCATTTTA AAACTGAAAA CCAAATCTAA ACCCGAATAG ACCAAATTGT TGGTTTATTC    1680

GGGTTTTTGG GTTCGGATTC GGTTTCTAAA TATGCTATAT TTTAGGGTAT AGGTTCGGGT    1740

TCAGTTTCTA ACCTTTAAAA CCTGAATAGA CGAATAACCC GAAATATAAA AAATCTCTTA    1800
```

-continued

```
ATATGTGATG ATATTATTAT ATGATTTATG AACTTATTAA CCGAAAATAA TGATACCATC    1860

CTAACGATAG TATATATATC TATGTATGCT ATTTTTATAG TCACTTGTTG TAATAATAGT    1920

ACTTCCAATT AATTAATCAG TGTATATATT TTAACAAAAG ATACTAGCCT CTCTACTATT    1980

TGAGTATATT CGGTGCACCG AATAGACCGA ACCGAAATTG TAAGTCTATT CAGGTTCGGT    2040

TCCTAAAATT ATTTTAAAAA TTTTGGTTCT CATATTTCAG AATCCGAAAT TTCATAAATC    2100

CAAATAGACC GAACCAAATT ACGCTAATAG ACCGAATAAC TAGCGTACTC GCAAGTCGCA    2160

CCCCACTAGC CTGCTGCGTG CGTAAGCGAG GACGTCACGC GTTCTCCCTC CCGTCGACCA    2220

AATACACTTG GTCTTCTAGC ACCTTCTTCC TCTCCAAGAC TCCAATCCCC CAACCACCAG    2280

AACCAGCGCC AGCTCTAACG TCACCTCTGA TTTCTCTCTC CTCTCTATTG CTAGCTGCTT    2340

TATTATAAGT AGCAGCTGCA GCAGGCAGGA GCTGCACACA CCCATCCAAT TCCAGCTGCT    2400

GATCTTGATC CTGCACCCCG AGCCGTACAC AAGAGCTAGT CGGTAGAACT TGCAGGAGCG    2460

GAGCAGAACT AAGTGCAGAG AACAGGACAT ATG                                2493

(2) INFORMATION FOR SEQ ID NO: 4:

(i) SEQUENCE CHARACTERISTICS:
        (A) LENGTH: 4201 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Arabidopsis thaliana
        (B) STRAIN: Landsberg erecta (viii) POSITION IN GENOME:
        (B) MAP POSITION: chromosome 5

(xi) SEQUENCE DESCRIPTION: SEQ ID NO: 4:

GAATTCATGT ACCAAATCAA TACTTTTTAG CCATAAATGA GTCAGTTTTA GTATCCACAT      60

GAATTTACCT ACCAGAGTGT TGTAAATTAT GTTCTTTTGG GGCCACTTAC ATGGATCTCA     120

TTCATTCACT GCAGCGAGTT CTCAGACCAC CAGAAAATTT ATTCAGTGAT CTGTTTTGAT     180

CATGCAACAT AAACTTATAA GCCACACAAG CAAAACAAAG ATATCCCATG TTGCATATAA     240

TACGAGCTAG CATATCATAA AGAAGGAAAC TTGAAGTAGC AAAGTTTCTA CTAAATTTCT     300

TGTCAGGAAT TTTTAAAATG CAATGACAAC CACTTGGAGC ACTATGAGTT TCAGAGCCAA     360

TAGAATGTTA CTATTTGGTG TGGATTCGAG CTAGCACGTG AAAGTGCATA AAAGTGATTA     420

CCTTTTGCCA AAGGTCACTG CACTTTTCCT CAGATAGTTT CTCACAGCCA TGGAAAGTGG     480

AGAATCCGCA TAAACGTACA ATTACAAGCT TTATATGGTC CCTCGACTCT TATTCTCTTC     540

TCAGTCTTTG CAACTAAATA GGGTTTTCGT TAATCTGAAA GAAGCAAAGT ATTCGAAACC     600

ACGGAAACCT GATAAAGAAT GAAAACAAAT AAGCAATAGT GTTTTCTTGA AAATCTCGAT     660

GCAACTTTGA GGATATTGTT ACATATGATC TATTACTCGT AACAGTTATC CGAAGGCCTA     720

CACATGTGAG AGAAGTTCCA AACCGCTACA ACAATAAACT TAATTAGAGA CTGTCAACGA     780

GCAATAATAA GCAAAACTAC TTTTTTCTTG AGCTACAAGT GAAAAGGCCA ATACACAATT     840

TACTCTTCAT GAACTCGAAC CACGTTACAA TCTCCAAAAA ATTTCATCAC CAAAGCACTA     900

AAAGCCAAAG ATGCCTCAAC TTATCCAACT TGGCAGGATA AAGATCTCCA AAAATGCTTA     960

CTAAAGAACC TAGAATCTTT TCTTTAGAAT TCAATGATCA TATAACCATT TCATAACAAT    1020

TCTAAATGCC ATTACATTCA TCGTAAAACC AGTAAATAAC AAGAACTTGT ATGTTAAGTT    1080
```

-continued

```
CCAATTACCA AGCAAAAAAA AACTTTTCAA AGTTTAAAGT TCAAAATGGG AAAGAGAAGT    1140

GCGGTGTAAG CAAATATGAA AGAGGAAGAG ATGCGAAAAG TGTATCCTAG GACCAGCATT    1200

TTATACAAAA AAAAAACACT CACTTTTCAG CTCTTAAGGC ATAGAGTGAA GGTAGCCATA    1260

TGAATTTGGC CACTAGAGCG TCCGTCAAAT CTCATTCTTT TTGGACCACA TAATGGGTAT    1320

CATACATTCA CTGGACCCAA AAGCGTAACT GGAGCTAGTC CTCAAACCTA GAGAGTATCG    1380

TATCCTGTAG CTTCCACATA GTAAACATTA TGAGCATAAC ACCAACAAGG CAACTCCAAG    1440

TACTAATGGT TATTAGTACA GGAAAACCCA CGATGCTAAA CACATGAATG GGTCACCAAA    1500

TAGAGTGAAG ATGGTTAAAT TGCATCTATG GATCATGTGG ACTAGTAAAT GAGTGTAGCA    1560

GAAAACTTCA CAATTACCTC TGTGATCTTA GAAACATGTC CTGAAAATTC CATACAAGTG    1620

TCGTTTGTAT TAGATTACTT CCACAGGTTG AGATCTAATA AAGCTACAAT AAATAGTATA    1680

GAGTATCATC ATAAACCCAA ATTACAGAGA TGTGACAACA CTCATGAGTC ATGTTTTGTA    1740

ACTACTTACT ATAATGGTTA CCAAGTGCAA ATTTCTACAT ACTATATATG ATAAATCTAA    1800

TTATTGCTCA TGTGGACTCC AAAATGCCTT TTAAGTTTTA ACTTGTGCGT CAGGTAAATT    1860

CTAATTTGTA GTCTCAAGAC TACTTGGCGG ATTCGAGTTT GATCCTAGAA AATCCACCGT    1920

CTCTATGTTT TTCATGTCAC TTTTCCGATA TGATTCTCAT TACCATGACT TTATGAACCA    1980

GATTAAACAT TATAACACTT TTCATCAGAA AATCCTTCGA AAGTTTCAAT TGCAAATCTT    2040

TCTAAATGAT GCAGATGCAT TCACAAATAA TGGAACAACA ACTATACCAT ATTCACGAGT    2100

TTGTCTAACC TTTGTATAGG TAGTCAACCC ATAACAGTTG GTGATGGCTC TGACACTCGA    2160

AGCCTTACTC GGAGAGATAC CTGAACAGTA ATCACAAGGT TCAGGATGAA TATTCAACCA    2220

CTTAAACTTT GTATAAAGCC AAAGAGATAA AACGAATCTA GCTTTACTTT AAATAAAATG    2280

CATATGAAAA TAGTAAAAGG TGATACGAAA AAATAGTAAC AATTTGCCTG CAACACCATG    2340

GCATTATCCG GACCACTTCC TCTTGAGAAT CTCAGTATGG CAAGTGGCAA AACCTAAGCA    2400

ACTTGTGAAC GGGTCCCAAC GAAGAAGTGC ATAGGAGGAG ATGTTTACAC TTTACACTTT    2460

ACACTTTACA CTTTACACAT AGGCCTTCCC AAAAGCTCAA CTAGCTGCAA GAGGATCCAA    2520

TAACATGTAA GAGCCACTAA CGCTGTGCCA CGTGTAGGCA CTCAGGATTC GATCTTCCCC    2580

TCTACTTATT CTCTCACACC AGATATAAGC TTTATTAGCC CCTTCTTTCA GATACCAGCT    2640

CCCACACCAT CAAACTTACT ACATCTGAGT TATTATGTTG AAACAAGAGA GTAACGACAT    2700

AGGTAGTGGA GAGAACAACA GGGCACGACC CTGTGACACA TGCCGGTCAA ACGCCTGCAC    2760

CGTGTATTGC CATGCAGATT CTGCCTACTT GTGCATGAGC TGTGATGCTC AAGTTCACTC    2820

TGCCAATCGC GTTGCTTCCC GCCATAAACG TGTCCGGGTC TGCGAGTCAT GTGAGCGTGC    2880

TCCGGCTGCT TTTTTGTGTG AGGCAGATGA TGCCTCTCTA TGCACAGCCT GTGATTCAGA    2940

GGTTCATTCT GCAAACCCAC TTGCTAGACG CCATCAGCGA GTTCCAATTC TACCAATTTC    3000

TGGAAACTCT TTCAGCTCCA TGACCACTAC TCACCACCAA AGCGAGAAAA CAATGACCGA    3060

TCCAGAGAAG AGACTGGTGG TGGATCAAGA GGAAGGTGAA GAAGGTGATA AGGATGCCAA    3120

GGAGGTTGCT TCGTGGCTGT TCCCTAATTC AGACAAAAAT AACAATAACC AAAACAATGG    3180

GTTATTGTTT AGTGATGAGT ATCTAAACCT TGTGGATTAC AACTCGAGTA TGGACTACAA    3240

ATTCACAGGT GAATACAGTC AACACCAACA AAACTGCAGC GTACCACAGA CGAGCTACGG    3300

GGGAGATAGA GTTGTTCCGC TTAAACTTGA AGAATCAAGG GGCCACCAGT GCCATAACCA    3360

ACAGAATTTT CAGTTCAATA TCAAATATGG CTCCTCAGGG ACTCACTACA ACGACAATGG    3420
```

```
TTCCATTAAC CATAACGTAA GGCTTTTGTA TATTTGTTAC CCCTTCAATT TAGCATCTTC    3480

CCATAACGCA GCAGGGTGAA TTCTTTCATC ATACACACAA ATCCACTGAT CCACTGCCAA    3540

CAGTTGATCT ATAGCACATA GAAATTTCAC CAGAAGTCTA TAATAAAAAC AATATATGCT    3600

TCCTTTTGCA TCGACTCTCT TTAGTCCTCT TACCAGGGGG ATTGAGAATG TCTTTGTTTC    3660

TGTCATTAGG CATACATTTC ATCCATGGAA ACTGGTGTTG TGCCGGAGTC AACAGCATGT    3720

GTCACAACAG CTTCACACCC AAGAACGCCC AAAGGGACAG TAGAGCAACA ACCTGACCCT    3780

GCAAGCCAGA TGATAACAGT AACACAACTC AGTCCAATGG ACAGAGAAGC CAGGGTCCTG    3840

AGATACAGAG AGAAGAGGAA GACAAGGAAA TTTGAGAAGA CAATAAGGTA TGCTTCGAGG    3900

AAGGCATATG CAGAGATAAG ACCGCGGGTC AATGGCCGGT TCGCAAAGAG AGAAATCGAA    3960

GCCGAGGAGC AAGGGTTCAA CACGATGCTA ATGTACAACA CAGGATATGG GATTGTTCCT    4020

TCATTCTGAT ACTCCTGTGG CAAAAAGAAA AACTAGATTG CAAGCTGTAA ATTACTTTTA    4080

GTTTGAGATT ATGTTAGGTT TGGTGAAATT CTTAGCTTCA AGAAGTATTA CTACTGTTGT    4140

GCAAATGGGT TTGTAGTTTT GGCTAATTAA AACTATAGTA TTCTTCTTTC TCTGCATTAG    4200

T                                                                   4201
```

(2) INFORMATION FOR SEQ ID NO: 5:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (vi) ORIGINAL SOURCE:
        (A) ORGANISM: Brassic napus (ix) FEATURE:
        (A) NAME/KEY: CDS
        (B) LOCATION:1..1098

(xi) SEQUENCE DESCRIPTION: SEQ ID NO: 5:

```
ATG TTC AAA CAA GAG AGT AAC AAC ATT GGT AGT GAA GAG AAC AAC ACC     48
Met Phe Lys Gln Glu Ser Asn Asn Ile Gly Ser Glu Glu Asn Asn Thr
375                 380                 385

GGG GCG CGA GCT TGT GAC ACA TGC GGG TCA ACC ATC TGC ACC GTG TAC     96
Gly Ala Arg Ala Cys Asp Thr Cys Gly Ser Thr Ile Cys Thr Val Tyr
390                 395                 400                 405

TGC CAT GCT GAC TCC GCC TAC TTA TGC AAT AGC TGC GAT GCT CAA GTC    144
Cys His Ala Asp Ser Ala Tyr Leu Cys Asn Ser Cys Asp Ala Gln Val
                410                 415                 420

CAC TCT GCC AAT CGC GTT GCT TCC CGC CAT AAA AGG GTC AGA GTG TGC    192
His Ser Ala Asn Arg Val Ala Ser Arg His Lys Arg Val Arg Val Cys
            425                 430                 435

GAG TCA TGT GAG CGT GCC CCT GCT GCT TTT ATG TGT GAG GCA GAT GAT    240
Glu Ser Cys Glu Arg Ala Pro Ala Ala Phe Met Cys Glu Ala Asp Asp
        440                 445                 450

GTG TCT CTA TGC ACA GCC TGT GAT TCA GAG GTT CAC TCC GCA AAC CCT    288
Val Ser Leu Cys Thr Ala Cys Asp Ser Glu Val His Ser Ala Asn Pro
    455                 460                 465

CTT GCT AGA CGC CAT CAG CGA GTT CCA GTT GTG CCG ATA ACT GGA AAC    336
Leu Ala Arg Arg His Gln Arg Val Pro Val Val Pro Ile Thr Gly Asn
470                 475                 480                 485

TCT TGC AGC TCC TTG GCC ACC GCT AAC CAC ACA ACA GTG ACC GAG CCA    384
```

-continued

```
Ser Cys Ser Ser Leu Ala Thr Ala Asn His Thr Thr Val Thr Glu Pro
            490                 495                 500

GAG AAG AGA GTG GTG TTA GTT CAA GAG GAT GCC AAA GAG ACG GCT TCA         432
Glu Lys Arg Val Val Leu Val Gln Glu Asp Ala Lys Glu Thr Ala Ser
            505                 510                 515

TGG TTG TTC CCT AAA AAC AGT GAC AAT CAC AAC AAC AAC AAC CAG AAC         480
Trp Leu Phe Pro Lys Asn Ser Asp Asn His Asn Asn Asn Asn Gln Asn
            520                 525                 530

AAT GAG TTG TTG TTT AGT GAT GAC TAT CTA GAC CTT GCT GAT TAC AAC         528
Asn Glu Leu Leu Phe Ser Asp Asp Tyr Leu Asp Leu Ala Asp Tyr Asn
    535                 540                 545

TCG AGT ATG GAC TAC AAG TTC ACT GGT CAA TAC AAT CAA CCT ACT CAA         576
Ser Ser Met Asp Tyr Lys Phe Thr Gly Gln Tyr Asn Gln Pro Thr Gln
550                 555                 560                 565

CAT AAA CAA GAC TGC ACC GTA CCA GAG AAA AAC TAC GGT GGA GAT AGA         624
His Lys Gln Asp Cys Thr Val Pro Glu Lys Asn Tyr Gly Gly Asp Arg
                570                 575                 580

GTT GTT CCA CTC CAA CTT GAA GAA ACA AGA GGA AAC TTG CAC CAC AAG         672
Val Val Pro Leu Gln Leu Glu Glu Thr Arg Gly Asn Leu His His Lys
            585                 590                 595

CAA CAT AAT ATC ACG TAT GGC TCC TCA GGA AGT CAC TAC AAC AAC AAT         720
Gln His Asn Ile Thr Tyr Gly Ser Ser Gly Ser His Tyr Asn Asn Asn
            600                 605                 610

GGT TCC ATA AAC CAT AAC GCA TAC AAT CCA TCA ATG GAA ACT GAC TTT         768
Gly Ser Ile Asn His Asn Ala Tyr Asn Pro Ser Met Glu Thr Asp Phe
    615                 620                 625

GTT CCG GAG CAG ACA GCA CCT GAC AAA ACA GTT TCA CAT CCA AAA ACG         816
Val Pro Glu Gln Thr Ala Pro Asp Lys Thr Val Ser His Pro Lys Thr
630                 635                 640                 645

CAC AAA GGG AAG ATA GAG AAA CTA CCT GAA CCT CTA ATT CAG ATT CTC         864
His Lys Gly Lys Ile Glu Lys Leu Pro Glu Pro Leu Ile Gln Ile Leu
                650                 655                 660

AGT CCA ATG GAC AGA GAA GCT AGA GTC CTG AGA TAC AGA GAG AAG AAG         912
Ser Pro Met Asp Arg Glu Ala Arg Val Leu Arg Tyr Arg Glu Lys Lys
            665                 670                 675

AAG AGA AGA AAG TTT GAG AAG ACA ATA AGG TAT GCT TCA AGG AAG GCA         960
Lys Arg Arg Lys Phe Glu Lys Thr Ile Arg Tyr Ala Ser Arg Lys Ala
            680                 685                 690

TAT GCA GAG AGA AGA CCG AGG ATC AAT GGA CGG TTT GCA AAG ATT AGT         1008
Tyr Ala Glu Arg Arg Pro Arg Ile Asn Gly Arg Phe Ala Lys Ile Ser
    695                 700                 705

GAA ACC GAA GTA GAG GAC CAA GAG TAC AAC ACA ATG CTA ATG TAC TAT         1056
Glu Thr Glu Val Glu Asp Gln Glu Tyr Asn Thr Met Leu Met Tyr Tyr
710                 715                 720                 725

GAC ACA GGA TAT GGC ATT GTT CCT TCA TTC TAT GGC CAA AAA                 1098
Asp Thr Gly Tyr Gly Ile Val Pro Ser Phe Tyr Gly Gln Lys
                730                 735

TAA                                                                     1101
```

(2) INFORMATION FOR SEQ ID NO: 6:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Phe Lys Gln Glu Ser Asn Asn Ile Gly Ser Glu Glu Asn Asn Thr
1               5                   10                  15
```

Gly Ala Arg Ala Cys Asp Thr Cys Gly Ser Thr Ile Cys Thr Val Tyr
            20                  25                  30

Cys His Ala Asp Ser Ala Tyr Leu Cys Asn Ser Cys Asp Ala Gln Val
        35                  40                  45

His Ser Ala Asn Arg Val Ala Ser Arg His Lys Arg Val Arg Val Cys
    50                  55                  60

Glu Ser Cys Glu Arg Ala Pro Ala Ala Phe Met Cys Glu Ala Asp Asp
65                  70                  75                  80

Val Ser Leu Cys Thr Ala Cys Asp Ser Glu Val His Ser Ala Asn Pro
                85                  90                  95

Leu Ala Arg Arg His Gln Arg Val Pro Val Pro Ile Thr Gly Asn
                100                 105                 110

Ser Cys Ser Ser Leu Ala Thr Ala Asn His Thr Thr Val Thr Glu Pro
            115                 120                 125

Glu Lys Arg Val Val Leu Val Gln Glu Asp Ala Lys Glu Thr Ala Ser
        130                 135                 140

Trp Leu Phe Pro Lys Asn Ser Asp Asn His Asn Asn Asn Asn Gln Asn
145                 150                 155                 160

Asn Glu Leu Leu Phe Ser Asp Asp Tyr Leu Asp Leu Ala Asp Tyr Asn
                165                 170                 175

Ser Ser Met Asp Tyr Lys Phe Thr Gly Gln Tyr Asn Gln Pro Thr Gln
                180                 185                 190

His Lys Gln Asp Cys Thr Val Pro Glu Lys Asn Tyr Gly Gly Asp Arg
                195                 200                 205

Val Val Pro Leu Gln Leu Glu Glu Thr Arg Gly Asn Leu His His Lys
        210                 215                 220

Gln His Asn Ile Thr Tyr Gly Ser Ser Gly Ser His Tyr Asn Asn Asn
225                 230                 235                 240

Gly Ser Ile Asn His Asn Ala Tyr Asn Pro Ser Met Glu Thr Asp Phe
                245                 250                 255

Val Pro Glu Gln Thr Ala Pro Asp Lys Thr Val Ser His Pro Lys Thr
                260                 265                 270

His Lys Gly Lys Ile Glu Lys Leu Pro Glu Pro Leu Ile Gln Ile Leu
        275                 280                 285

Ser Pro Met Asp Arg Glu Ala Arg Val Leu Arg Tyr Arg Glu Lys Lys
        290                 295                 300

Lys Arg Arg Lys Phe Glu Lys Thr Ile Arg Tyr Ala Ser Arg Lys Ala
305                 310                 315                 320

Tyr Ala Glu Arg Arg Pro Arg Ile Asn Gly Arg Phe Ala Lys Ile Ser
                325                 330                 335

Glu Thr Glu Val Glu Asp Gln Glu Tyr Asn Thr Met Leu Met Tyr Tyr
                340                 345                 350

Asp Thr Gly Tyr Gly Ile Val Pro Ser Phe Tyr Gly Gln Lys
                355                 360                 365

(2) INFORMATION FOR SEQ ID NO: 7:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (vi) ORIGINAL SOURCE:
    (A) ORGANISM: Brassica napus (ix) FEATURE:
    (A) NAME/KEY: CDS
    (B) LOCATION:1..1098

(xi) SEQUENCE DESCRIPTION: SEQ ID NO: 7:

| | | | | | | | | | | | | | | | | |
|---|---|---|---|---|---|---|---|---|---|---|---|---|---|---|---|---|
| ATG | TTC | AAA | CAA | GAG | AGT | AAC | AAC | ATT | TGT | AAT | AGA | GAG | AAC | AAC | AGA | 48 |
| Met | Phe | Lys | Gln | Glu | Ser | Asn | Asn | Ile | Cys | Asn | Arg | Glu | Asn | Asn | Arg | |
| | | | | 370 | | | | 375 | | | | 380 | | | | |
| GGG | GCA | CGA | GCC | TGT | GAC | ACA | TGC | GGG | TCA | ACC | ATC | TGC | ACC | GTG | TAC | 96 |
| Gly | Ala | Arg | Ala | Cys | Asp | Thr | Cys | Gly | Ser | Thr | Ile | Cys | Thr | Val | Tyr | |
| | | | 385 | | | | 390 | | | | 395 | | | | | |
| TGC | CAT | GCT | GAC | TCT | GCC | TAC | TTA | TGC | AAT | AGC | TGC | GAT | GCT | CAA | GTC | 144 |
| Cys | His | Ala | Asp | Ser | Ala | Tyr | Leu | Cys | Asn | Ser | Cys | Asp | Ala | Gln | Val | |
| | | | 400 | | | | 405 | | | | 410 | | | | | |
| CAC | TCT | GCC | AAT | CGC | GTT | GCT | TCC | CGC | CAT | AAA | CGT | GTC | CGG | GTC | TGC | 192 |
| His | Ser | Ala | Asn | Arg | Val | Ala | Ser | Arg | His | Lys | Arg | Val | Arg | Val | Cys | |
| 415 | | | | 420 | | | | 425 | | | | | | | 430 | |
| GAG | TCA | TGT | GAG | CGT | GCC | CCT | GCT | GCT | TTT | ATG | TGT | GAG | GCA | GAT | GAT | 240 |
| Glu | Ser | Cys | Glu | Arg | Ala | Pro | Ala | Ala | Phe | Met | Cys | Glu | Ala | Asp | Asp | |
| | | | | 435 | | | | 440 | | | | 445 | | | | |
| GTG | TCT | CTA | TGC | ACA | GCC | TGT | GAT | TTA | GAG | GTT | CAC | TCC | GCA | AAC | CCT | 288 |
| Val | Ser | Leu | Cys | Thr | Ala | Cys | Asp | Leu | Glu | Val | His | Ser | Ala | Asn | Pro | |
| | | | 450 | | | | 455 | | | | 460 | | | | | |
| CTT | GCT | AGA | CGC | CAT | CAG | CGA | GTT | CCA | GTT | GTG | CCG | ATA | ATT | GGA | AAC | 336 |
| Leu | Ala | Arg | Arg | His | Gln | Arg | Val | Pro | Val | Val | Pro | Ile | Ile | Gly | Asn | |
| | | | 465 | | | | 470 | | | | 475 | | | | | |
| TCT | TGC | AGC | TCC | TTG | GCC | ACC | GCT | AAC | CAC | ACA | ACA | GTG | ACC | GAG | CCA | 384 |
| Ser | Cys | Ser | Ser | Leu | Ala | Thr | Ala | Asn | His | Thr | Thr | Val | Thr | Glu | Pro | |
| | 480 | | | | 485 | | | | 490 | | | | | | | |
| GAG | AAG | AGA | GTG | GTG | TTA | GTT | CAA | GAG | GAT | GCC | AAA | GAG | ACG | GCT | TCA | 432 |
| Glu | Lys | Arg | Val | Val | Leu | Val | Gln | Glu | Asp | Ala | Lys | Glu | Thr | Ala | Ser | |
| 495 | | | | 500 | | | | 505 | | | | | | | 510 | |
| TGG | TTG | TTC | CCT | AAA | AAC | AGT | GAC | TAT | CAC | AAC | AAC | AAC | AAC | AAC | CAG | 480 |
| Trp | Leu | Phe | Pro | Lys | Asn | Ser | Asp | Tyr | His | Asn | Asn | Asn | Asn | Asn | Gln | |
| | | | | 515 | | | | 520 | | | | 525 | | | | |
| AAC | AAT | GAG | TTG | TTG | TTT | AGT | GAT | GAC | TAC | CTA | GAC | CTT | GCT | GAT | TAC | 528 |
| Asn | Asn | Glu | Leu | Leu | Phe | Ser | Asp | Asp | Tyr | Leu | Asp | Leu | Ala | Asp | Tyr | |
| | | | 530 | | | | 535 | | | | 540 | | | | | |
| AAC | TCC | AGT | ATG | GAC | TAC | AAG | TTC | ACC | AGT | CAA | TAC | AAT | CAA | CCT | CGA | 576 |
| Asn | Ser | Ser | Met | Asp | Tyr | Lys | Phe | Thr | Ser | Gln | Tyr | Asn | Gln | Pro | Arg | |
| | | | 545 | | | | 550 | | | | 555 | | | | | |
| CAT | AAA | CAA | GAC | TGC | ATC | GTA | CCA | GAG | AAA | AAC | TAC | AGT | GGA | GAT | AGA | 624 |
| His | Lys | Gln | Asp | Cys | Ile | Val | Pro | Glu | Lys | Asn | Tyr | Ser | Gly | Asp | Arg | |
| | | | 560 | | | | 565 | | | | 570 | | | | | |
| GTT | GTT | CCG | CTC | CAA | CTT | GAA | GAA | ACA | AGA | GGA | AAC | TTG | CGG | AAC | AAG | 672 |
| Val | Val | Pro | Leu | Gln | Leu | Glu | Glu | Thr | Arg | Gly | Asn | Leu | Arg | Asn | Lys | |
| 575 | | | | 580 | | | | 585 | | | | | | | 590 | |
| CAA | CAG | AAT | ATC | ACA | TAT | GGC | TCC | TCA | GGA | AGC | CAA | TAC | AAC | AAC | AAC | 720 |
| Gln | Gln | Asn | Ile | Thr | Tyr | Gly | Ser | Ser | Gly | Ser | Gln | Tyr | Asn | Asn | Asn | |
| | | | | 595 | | | | 600 | | | | 605 | | | | |
| GGT | TCC | ATT | AAC | CAT | AAC | GCA | TAC | AAT | CCA | TCA | ATG | GAA | ACT | GAC | TTT | 768 |
| Gly | Ser | Ile | Asn | His | Asn | Ala | Tyr | Asn | Pro | Ser | Met | Glu | Thr | Asp | Phe | |
| | | | 610 | | | | 615 | | | | 620 | | | | | |
| GTG | CCG | GAG | CAG | ACA | GCA | CCT | GAC | ACA | ACA | GTT | TCA | CAT | CCA | AAA | ACG | 816 |
| Val | Pro | Glu | Gln | Thr | Ala | Pro | Asp | Thr | Thr | Val | Ser | His | Pro | Lys | Thr | |
| | | | 625 | | | | 630 | | | | 635 | | | | | |
| CAC | AAA | GGG | AAG | ACA | GCA | CAA | CTA | CCT | GAA | CCT | CTA | ATT | CAG | ATT | CTC | 864 |

```
His Lys Gly Lys Thr Ala Gln Leu Pro Glu Pro Leu Ile Gln Ile Leu
        640                 645                 650

AGT CCA ATG GAC AGA GAA GCT AGA GTC CTG AGA TAC AGA GAG AAG AAG      912
Ser Pro Met Asp Arg Glu Ala Arg Val Leu Arg Tyr Arg Glu Lys Lys
655                 660                 665                 670

AAG AGA AGA AAG TTT GAG AAG ACA ATA AGG TAT GCT TCA AGG AAG GCA      960
Lys Arg Arg Lys Phe Glu Lys Thr Ile Arg Tyr Ala Ser Arg Lys Ala
                675                 680                 685

TAT GCA GAG AGA AGA CCG AGG ATA AAT GGA CGG TTT GCA AAG ATG AGT     1008
Tyr Ala Glu Arg Arg Pro Arg Ile Asn Gly Arg Phe Ala Lys Met Ser
        690                 695                 700

GAA ACC GAA GTA GAG GAC CAA GAG TAC AAC ACA ATG CTA ATG TAC TGC     1056
Glu Thr Glu Val Glu Asp Gln Glu Tyr Asn Thr Met Leu Met Tyr Cys
705                 710                 715

GAC ACA GGA TAT GGC ATT GTT CCT TCA TTC TAT GGC CAA AAA             1098
Asp Thr Gly Tyr Gly Ile Val Pro Ser Phe Tyr Gly Gln Lys
        720                 725                 730

TAA                                                                  1101

(2) INFORMATION FOR SEQ ID NO: 8:

(i) SEQUENCE CHARACTERISTICS:
            (A) LENGTH: 366 amino acids
            (B) TYPE: amino acid
            (D) TOPOLOGY: linear (ii) MOLECULE TYPE: protein (xi) SEQUENCE DESCRIPTION: SEQ ID NO: 8:

Met Phe Lys Gln Glu Ser Asn Asn Ile Cys Asn Arg Glu Asn Arg
  1               5                  10                  15

Gly Ala Arg Ala Cys Asp Thr Cys Gly Ser Thr Ile Cys Thr Val Tyr
              20                  25                  30

Cys His Ala Asp Ser Ala Tyr Leu Cys Asn Ser Cys Asp Ala Gln Val
          35                  40                  45

His Ser Ala Asn Arg Val Ala Ser Arg His Lys Arg Val Arg Val Cys
     50                  55                  60

Glu Ser Cys Glu Arg Ala Pro Ala Ala Phe Met Cys Glu Ala Asp Asp
 65                  70                  75                  80

Val Ser Leu Cys Thr Ala Cys Asp Leu Glu Val His Ser Ala Asn Pro
                 85                  90                  95

Leu Ala Arg Arg His Gln Arg Val Pro Val Val Pro Ile Ile Gly Asn
             100                 105                 110

Ser Cys Ser Ser Leu Ala Thr Ala Asn His Thr Thr Val Thr Glu Pro
         115                 120                 125

Glu Lys Arg Val Val Leu Val Gln Glu Asp Ala Lys Glu Thr Ala Ser
     130                 135                 140

Trp Leu Phe Pro Lys Asn Ser Asp Tyr His Asn Asn Asn Asn Asn Gln
145                 150                 155                 160

Asn Asn Glu Leu Leu Phe Ser Asp Asp Tyr Leu Asp Leu Ala Asp Tyr
                165                 170                 175

Asn Ser Ser Met Asp Tyr Lys Phe Thr Ser Gln Tyr Asn Gln Pro Arg
            180                 185                 190

His Lys Gln Asp Cys Ile Val Pro Glu Lys Asn Tyr Ser Gly Asp Arg
        195                 200                 205

Val Val Pro Leu Gln Leu Glu Gly Thr Arg Gly Asn Leu Arg Asn Lys
    210                 215                 220
```

```
Gln Gln Asn Ile Thr Tyr Gly Ser Ser Gly Ser Gln Tyr Asn Asn Asn
225                 230                 235                 240

Gly Ser Ile Asn His Asn Ala Tyr Asn Pro Ser Met Glu Thr Asp Phe
            245                 250                 255

Val Pro Glu Gln Thr Ala Pro Asp Thr Thr Val Ser His Pro Lys Thr
            260                 265                 270

His Lys Gly Lys Thr Ala Gln Leu Pro Glu Pro Leu Ile Gln Ile Leu
            275                 280                 285

Ser Pro Met Asp Arg Glu Ala Arg Val Leu Arg Tyr Arg Glu Lys Lys
290                 295                 300

Lys Arg Arg Lys Phe Glu Lys Thr Ile Arg Tyr Ala Ser Arg Lys Ala
305                 310                 315                 320

Tyr Ala Glu Arg Arg Pro Arg Ile Asn Gly Arg Phe Ala Lys Met Ser
                325                 330                 335

Glu Thr Glu Val Glu Asp Gln Glu Tyr Asn Thr Met Leu Met Tyr Cys
            340                 345                 350

Asp Thr Gly Tyr Gly Ile Val Pro Ser Phe Tyr Gly Gln Lys
            355                 360                 365
```

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer used for PCR"

(vi) ORIGINAL SOURCE:
        (A) ORGANISM: yeast (xi) SEQUENCE DESCRIPTION: SEQ ID NO: 9:

TCCTGCTCGC TTCGCTACTT        20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer used for PCR"

(vi) ORIGINAL SOURCE:
        (A) ORGANISM: yeast (xi) SEQUENCE DESCRIPTION: SEQ ID NO: 10:

GCGATGCTGT CGGAATGGAC        20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer used for PCR"

(vi) ORIGINAL SOURCE:
        (A) ORGANISM: yeast (xi) SEQUENCE DESCRIPTION: SEQ ID NO: 11:

AAGTACTCTC GGTAGCCAAG                                                    20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for pcr"

(vi) ORIGINAL SOURCE:
        (A) ORGANISM: yeast (xi) SEQUENCE DESCRIPTION: SEQ ID NO: 12:

GTGTGGTCGC CATGATCGCG                                                    20

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 13:

CTGGGAAGTG AATGGAGACA TA                                                 22

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 14:

AGGAGTCGCA TAAGGGAGAG                                                    20

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 15:

```
ACGTCGGATG CTCACTATAG GGATC                                                    25

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 16:

GTGATAAACT ACCGCATTAA AGC                                                      23

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 17:

ACGTCGGATG ACTTTAATTT ATTCACTA                                                 28

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 18:

GACGTGGATG CTCACTAAAG GGATC                                                    25

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 19:

AGAGCCTTCA ACCCAGTCAG                                                          20
```

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: yeast (xi) SEQUENCE DESCRIPTION: SEQ ID NO: 20:

ACGTCGGATG CCGATCTCAA GATTA                                    25

(2) INFORMATION FOR SEQ ID NO: 21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: Arabidopsis thaliana (xi) SEQUENCE DESCRIPTION: SEQ ID NO: 21:

GCTCCCACAC CATCAAACTT ACTAC                                    25

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: Arabidopsis thaliana (xi) SEQUENCE DESCRIPTION: SEQ ID NO: 22:

CTCCTCGGCT TCGATTTCTC                                          20

(2) INFORMATION FOR SEQ ID NO: 23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer used for PCR"

(vi) ORIGINAL SOURCE:
        (A) ORGANISM: designed primer not derived from any organism (xi) SEQUENCE DESCRIPTION: SEQ ID NO: 23:

GACTCGAGTC GACATCG                                             17

(2) INFORMATION FOR SEQ ID NO: 24:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthesised primer for
            PCR"

(vi) ORIGINAL SOURCE:
        (A) ORGANISM: Arabidopsis thaliana (xi) SEQUENCE DESCRIPTION: SEQ ID NO: 24:

TGCAGATTCT GCCTACTTGT GC                                             22

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthesised primer for
            PCR"

(vi) ORIGINAL SOURCE:
        (A) ORGANISM: Arabidopsis thaliana (xi) SEQUENCE DESCRIPTION: SEQ ID NO: 25:

TGATTCTGCC TACTTGTGCT C                                              21

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer synthesised for
            PCR"

(vi) ORIGINAL SOURCE:
        (A) ORGANISM: Arabidopsis thaliana (xi) SEQUENCE DESCRIPTION: SEQ ID NO: 26:

GCTTGGTTTG CCTCTTCATC                                                20

(2) INFORMATION FOR SEQ ID NO: 27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer synthesised for
            PCR"

(vi) ORIGINAL SOURCE:
        (A) ORGANISM: Arabidopsis thaliana (xi) SEQUENCE DESCRIPTION: SEQ ID NO: 27:

GGTCCCAACG AAGAAGTGC                                                 19

(2) INFORMATION FOR SEQ ID NO: 28:

-continued

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthesised primer for
            PCR"

(vi) ORIGINAL SOURCE:
        (A) ORGANISM: Arabidopsis thaliana (xi) SEQUENCE DESCRIPTION: SEQ ID NO: 28:

CAGGGAGGCG TGAAAGTGT                                                       19

(2) INFORMATION FOR SEQ ID NO: 29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "adapter synthesised to
            modify sequence for gene cloning"

(vi) ORIGINAL SOURCE:
        (A) ORGANISM: designed sequence not derived from any
            organism (xi) SEQUENCE DESCRIPTION: SEQ ID NO: 29:

TACAAGCTTG                                                                 10

(2) INFORMATION FOR SEQ ID NO: 30:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide
            synthesised to assist gene cloning"

(vi) ORIGINAL SOURCE:
        (A) ORGANISM: designed sequence, not derived from any
            organism (xi) SEQUENCE DESCRIPTION: SEQ ID NO: 30:

TATCGATAGT AC                                                              12

(2) INFORMATION FOR SEQ ID NO: 31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "primer used for PCR"

(vi) ORIGINAL SOURCE:
        (A) ORGANISM: yeast (xi) SEQUENCE DESCRIPTION: SEQ ID NO: 31:

TTCAAGCTCT ACGCCGGA                                                        18
```